US009138495B2

(12) United States Patent
Ballinger et al.

(10) Patent No.: US 9,138,495 B2
(45) Date of Patent: Sep. 22, 2015

(54) CONJUGATES AND THEIR USES IN MOLECULAR IMAGING

(75) Inventors: James Russell Ballinger, London (GB); David Berry, London (GB); Philip John Blower, London (GB); Yongmin Ma, Zhejiang (CN); Gregory Edgar David Mullen, London (GB)

(73) Assignee: King's College London, London (GB)

( * ) Notice: Subject to any disclaimer, the term of this patent is extended or adjusted under 35 U.S.C. 154(b) by 87 days.

(21) Appl. No.: 13/884,660

(22) PCT Filed: Nov. 11, 2011

(86) PCT No.: PCT/GB2011/001599
§ 371 (c)(1),
(2), (4) Date: Sep. 24, 2013

(87) PCT Pub. No.: WO2012/063028
PCT Pub. Date: May 18, 2012

(65) Prior Publication Data
US 2014/0056810 A1 Feb. 27, 2014

(30) Foreign Application Priority Data
Nov. 11, 2010 (GB) .................................. 1019118.7

(51) Int. Cl.
A61K 51/04 (2006.01)
A61K 51/08 (2006.01)
A61K 51/10 (2006.01)

(52) U.S. Cl.
CPC ......... *A61K 51/0455* (2013.01); *A61K 51/0478* (2013.01); *A61K 51/088* (2013.01); *A61K 51/1033* (2013.01)

(58) Field of Classification Search
CPC .............. A61K 51/00; A61K 51/0455; A61K 51/0478; A61K 51/088; A61K 51/1033
USPC ................ 424/1.65, 1.69, 9.32, 9.361, 9.364; 600/420, 427
See application file for complete search history.

(56) References Cited

U.S. PATENT DOCUMENTS

| 8,158,804 B2 | 4/2012 | Wadsworth et al. |
| 8,475,768 B2 | 7/2013 | Axelsson et al. |
| 2011/0092806 A1* | 4/2011 | Port et al. ...................... 600/420 |

FOREIGN PATENT DOCUMENTS

| WO | WO 97/00245 | 1/1997 |
| WO | WO 2008/085064 | 7/2008 |
| WO | WO 2009/021947 | 2/2009 |
| WO | WO2009021947 | * 2/2009 |

OTHER PUBLICATIONS

Hu, Shi-zhen, et al., "Minibody: A Novel Engineered Anti-Carcinoembryonic Antigen Antibody Fragment (Single-Chain Fv-CH3) Which Exhibits Rapid, High-Level Targeting of Xenografts", Cancer Research, vol. 56, Jul. 1, 1996, pp. 3055-3061.
Giersing, Birgitte K., et al., "Synthesis and Characterization of 111 In-DTPA-N-TIMP-2: A Radiopharmaceutical for Imaging Matrix Metalloproteinase Expression", Bioconjugate Chemistry, vol. 12, No. 6, Oct. 12, 2001, pp. 964-971.
Tavare, Richard, et al., "Efficient Site-Specific Radiolabeling of a Modified C2A Domain of Synaptotagmin I with [99mTc(C0)3]+: A New Radiopharmaceutical for Imaging Cell Death", Bioconjugate Chemistry, vol. 20, Oct. 29, 2009, pp. 2071-2081.
Velikyan, I., et al., "Convenient Preparation of 68Ga-Based PET-Radiopharmaceuticals at Room Temperature", Bioconjugate Chemistry, vol. 19, Jan. 19, 2008, pp. 569-573.
Hancock, Robert D., "Design of Ligands containing the o-Hydroxybenzyl Group. Metal-complexing Properties of N,N"-Bis(2-hydroxybenzyl)-diethylenetriamine-N,N', N"- triacetic Acid", Journal of the Chemical Society, Dalton Transactions, Jan. 1, 1994, pp. 2679-2685.
Emberson, Louise M., et al., "Expression of an anti-CD33 single-chain antibody by *Pichia pastoris*", Journal of Immunological Methods, vol. 305, No. 2, Jun. 16, 2005, pp. 135-151.
Reiter, Yoram, et al., "Engineering antibody Fv fragments for cancer detection and therapy: Disulfide-stabilized Fv fragments", Nature Biotechnology, vol. 14, Oct. 14, 1996, pp. 1239-1245.
Tait, Jonathan F., et al., "Measurement of the affinity and cooperativity of annexin V-membrane binding under conditions of low membrane occupancy", Analytical Biochemistry, vol. 329, Apr. 30, 2004, pp. 112-119.
Koop, B., et al., "Labelling of a monoclonal antibody with 68Ga using three DTPA-based bifunctional ligands and their in vitro evaluation for application in radioimmunotherapy", Radiochimica Acta, vol. 95, Jan. 2007, pp. 39-42.
Santos, M. Amelia, et al., "N-Carboxyalkyl derivativesd of 3-hydroxy-4-pyridinones: synthesis, complexation with Fe (III), Al (III) and Ga(III) and in vivo evaluation", Journal of Inorganic Biochemistry, vol. 92, Sep. 30, 2002, pp. 43-54.
Bird, Robert E., et al, "Single-Chain Antigen-Binding Proteins", American Association for the Advancement of Science, vol. 242, No. 4877, Oct. 21, 1988, pp. 423-426.
Newkome, George R., et al., "Cascade Polymers: Synthesis and Characterization of One-Directional Arborols Based on Adamantane", The Journal of Organic Chemistry, vol. 56, Dec. 1, 1991, pp. 7162-7167.
Huston, James S., et al., "Protein engineering of antibody binding sites: Recovery of specific activity in an anti-digoxin single-chain Fv analogue produced in *Escherichia coli*", Proceedings of the National Academy of Sciences of the United States of America, vol. 85, Aug. 15, 1988, pp. 5879-5883.

(Continued)

*Primary Examiner* — Michael G Hartley
*Assistant Examiner* — Jagadishwar Samala
(74) *Attorney, Agent, or Firm* — McCarter & English

(57) ABSTRACT

The present invention relates to bifunctional compounds, the bifunctional compounds for use in molecular imaging and therapy, methods of molecular imaging using the bifunctional compounds and kits including the bifunctional compounds for use molecular imaging. The bifunctional compounds have a tripodal hydroxypyridinone chelating portion and may be conjugated to a targeting group so that the compounds target specific cells or tissues in a subject.

27 Claims, 9 Drawing Sheets

(56) References Cited

OTHER PUBLICATIONS

Santos, M. Amelia "Recent developments on 3-hydroxy-4-pyridinones with respect to their clinical applications Mono and combined ligand approaches", Coordination Chemistry Reviews, vol. 252, Feb. 7, 2008, pp. 1213-1224.

Hajela, Sharad, et al., "A Tris-hydroxymethyl-Substituted Derivative of Gd-TREN-Me-3,2-HOPO: An MRI Relaxation Agent with Improved Efficiency", Journal of the American Chemical Society, vol. 122, Oct. 28, 2000, pp. 11228-11229.

Nunes, Ana, et al., "Fluorescent 3-hydroxy-4-pyridinone hexadentate iron chelators: intracellular distribution and the relevance to antimycobacterial properties", Journal of Biological Inorganic Chemistry, vol. 15, No. 6, Apr. 3, 2010, pp. 861-877.

Holliger, Philipp, et al., ""Diaboides": Small bivalent and bispecific antibody fragments", Proceedings of the National Acadmey of Sciences of the United States of America, vol. 90, Jul. 15, 1993, pp. 6444-6448.

Chaves, Silvia, et al., "A gallium complex with a new tripodal tris-hydroxypyridinone for potential nuclear diagnostic imaging: solution and in vivo studies of 67Ga-labeled species", Journal of Inorganic Biochemistry, vol. 105, Oct. 7, 2010, pp. 31-38.

Puerta, David T., et al., "Tris(pyrone) Chelates of Gd(III) as High Solubility MRI-CA", Journal of the American Chemical Society, vol. 128, No. 7, Feb. 1, 2006, pp. 2222-2223.

UKIPO Search Report relating to GB1019118.7 dated Feb. 10, 2011, 4 Pages.

Fernandes, Sofia Sousa, et al. "Identification of a new hexadentate iron chelator capable of restricting the intramacrophagic growth of *Mycobacterium avium*", Microbes and Infection, vol. 12, Jan. 25, 2010, pp. 287-294.

Zhou, Tao, et al., "Synthesis and Iron (III)-Chelating Properties of Novel 3-Hydroxypyridin-4-one Hexadentate Ligand-Containing Copolymers", Biomacromolecules, vol. 9, No. 5, Mar. 29, 2008, pp. 1372-1380.

Imbert, Daniel, et al., "Synthesis and iron (III) complexing ability of CacCAM, a new analog of enterobactin possessing a free carboxylic anchor arm. Comparative studies with TRENCAM", New Journal of Chemistry, vol. 24, Apr. 13, 2000, pp. 281-288.

Zhou, Tao, et al., "Iron Binding Dendrimers: A Novel Approach for the Treatment of Haemochromatosis", Journal of Medicinal Chemistry, vol. 49, Jun. 21, 2006, pp. 4171-4182.

Berry, David J., et al., "Efficient bifunctional gallium-68 chelators for positron emission tomography: tris (hydroxypyridinone) ligands", Chemical Communications, vol. 47, May 27, 2011, pp. 7068-7070.

Caravan, Peter, et al., "Gadolinium(III) Chelates as MRI Contrast Agents: Structure, Dynamics, and Applications", Chemical Reviews, vol. 99, No. 9, Aug. 20, 1999, pp. 2293-2352.

Ma, Yong Min, et al., "The selective quantification of iron by hexadentate fluorescent probes", Bioorganic & Medicinal Chemistry, vol. 17, No. 23, Oct. 8, 2009, pp. 8093-8101.

Burgess, John, et al., "Hydroxypyranones, Hydroxypyridinones, and Their Complexes", Advances in Inorganic Chemistry, vol. 60, Jul. 7, 2011, pp. 167-243.

Transmittal of International Search Report relating to PCT/GB2011/001599 dated Mar. 21, 2012.

Written Opinion of the International Searching Authority relating to PCT/GB2011/001599 dated Mar. 21, 2012.

* cited by examiner

CONJUGATES AND THEIR USES IN MOLECULAR IMAGING

RELATED APPLICATIONS

This application is a national stage application filed under 35 USC 371 of PCT/GB2011/001599, filed Nov. 11, 2011, which claims the benefit of GB Patent Application No. 1019118.7, filed Nov. 11, 2010, all of which are incorporated herein, in entirety, by reference.

FIELD OF THE INVENTION

The present invention relates to bifunctional compounds and in particular compounds for use in molecular imaging and therapy. The compounds may be conjugated to a targeting group so that the compounds target specific cells or tissues in a subject.

BACKGROUND OF THE INVENTION

Molecular imaging may be defined as the three-dimensional mapping of molecular processes, such as gene expression, blood flow, physiological changes (pH, $[O_2]$ etc.), immune responses, and cell trafficking, in vivo. It can be used to detect and diagnose disease, select optimal treatments, and to monitor the effects of treatments to obtain an early readout of efficacy. A number of distinct technologies can in principle be used for molecular imaging, including positron emission tomography (PET), single photon emission tomography (SPET), optical (OI) and magnetic resonance imaging (MRI). Combinations of these modalities are emerging to provide improved clinical applications, e.g. PET/CT and SPET/CT ("multi-modal imaging").

Radionuclide imaging with PET and SPET has the advantage of extremely high sensitivity and small amounts of administered contrast agents (e.g. picomolar in vivo), which do not perturb the in vivo molecular processes. Moreover, the targeting principles for radionuclide imaging can be applied also in targeted delivery of radionuclide therapy. Typically the isotope that is used as a radionuclide in molecular imaging is incorporated into a molecule to produce a radiotracer that is pharmaceutically acceptable to the subject. Many radiotracers have been developed with a range of properties. For example, fluorodeoxyglucose ($^{18}F$) is a labelled glucose derivative that is frequently used in molecular imaging with PET.

WO 2009/021947 describes tripodal chelators for use as MRI contrast agents. Hydroxypyridinone chelating groups with a hydrophilic R group are described. The hydrophilic group is required to help solubilise the chelator. In addition, the chelator may be coupled to large molecules, such as a dendrimer, in order to increase the relaxivity of the MRI contrast agent.

SUMMARY OF THE INVENTION

It may be difficult to prepare radiotracers with sensitive functional moieties. For example, incorporation of radioisotopes into the radiotracer may involve elevated temperatures that would disrupt protein structure. It may be desirable to include sensitive functional moieties into radiotracers and so it is a need to provide radiotracers that may be prepared using mild conditions. As a result imaging conjugates with improved functionality and improved molecular imaging properties may be produced.

Currently, 1,4,7,10-tetraazacyclododecane-N,N',N",N"'-tetraacetic acid (DOTA) is a common chelator for gallium-68 (and other metallic radioisotopes such as Ga-67, In-111, Cu-64, Lu-177, Y-90) used in molecular imaging and targeted radionuclide therapy. However, DOTA has a long radiolabelling time of around 30 minutes (relative to the half-life of $^{68}Ga$~68 minutes). In addition, chelation of gallium by DOTA derivatives often requires a high labelling temperature of around 95° C. The present inventors have found bifunctional molecules that are able to quickly chelate radionuclides at room temperature, whilst retaining adequate or even enhanced stability towards dissociation in the biological milieu. In addition to the metal chelating portion, the bifunctional molecules have a reactive portion to couple the bifunctional molecule to a functional moiety, such as targeting group which can target, for example, cells, tissues or biological molecules in the body.

At its most general, the present invention provides bifunctional molecules for molecular imaging having a tripodal hexadentate tris(hydroxypyridinone) chelating portion to couple to a radionuclide or an imaging label and a reactive functionality to couple to a targeting group for targeting specific cells or tissues in a subject or to a delivery vehicle for delivering a drug, toxin or other such molecule so that the in vivo distribution and/or final location of the target group or delivery vehicle may be monitored.

Accordingly, in a first aspect the present invention provides a bifunctional compound for use in a method of molecular imaging, wherein the bifunctional compound is represented by the formula:

or salts thereof;

wherein one of X and Y is C=O and the other is NR;

wherein each m and p are independently selected from 0 to 6;

wherein $R^1$ is a chelating group capable of chelating a radionuclide and is selected from:

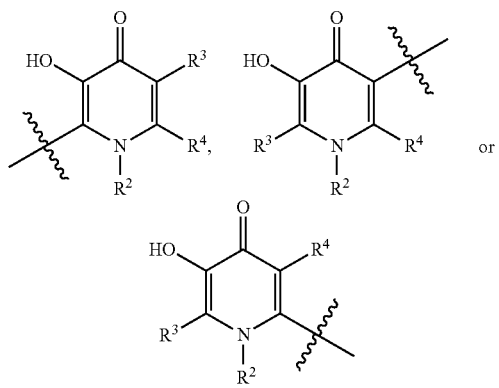

wherein R, $R^2$, $R^3$ and $R^4$ are independently hydrogen or an optionally substituted $C_{1-7}$ alkyl group;

B is a linker group for linking the chelating group to the reactive group, wherein is represented by the formula:

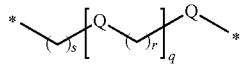

wherein each Q is independently selected from a group consisting of —NR$^5$—, —C(O)NR$^5$—, —C(O)O—, —NR$^5$C(O)NR$^5$—, —NR$^5$C(S)NR$^5$— and —O—, each R$^5$ is independently hydrogen or an optionally substituted C$_{1-7}$ alkyl group, each q and s are independently selected from 0 to 6 and each r is independently selected from 1 to 6;

A* is a reacted reactive group that is coupled to T, T being a targeting group capable of binding to a target of interest in the subject;

wherein the method comprises the steps of:
(a) administering the bifunctional compound to the subject so that the bifunctional compound binds to the target of interest; and
(b) administering an imaging probe composition comprising a radionuclide to the subject, so that the chelating group R$^1$ of the bifunctional compound chelates the radionuclide at the target of interest; and
(c) detecting the radionuclide to image the target of interest in the biological system.

The bifunctional compound of the first aspect may circulate the biological system to a targeted location. Then, when the radionuclide is introduced into the subject, the radionuclide may quickly pass though the system and chelate with the bifunctional compound. In this way, the radionuclide may be fixed in a location of interest within a short time of being introduced into the biological system so that the efficacy of the radionuclide is maximised.

Preferably s is independently selected from 0 to 6, each r is independently selected from 1 to 6, and q is selected from 1 to 6.

Preferably the method of molecular imagining is PET or SPET.

In another aspect, the present invention provides a bifunctional compound for chelating a radionuclide for use in molecular imaging, wherein the compound is represented by the formula:

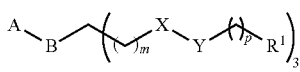

or salts thereof;
wherein one of X and Y is C═O and the other is NR;
wherein each m and p are independently selected from 0 to 6;
wherein R$^1$ is a chelating group selected from:

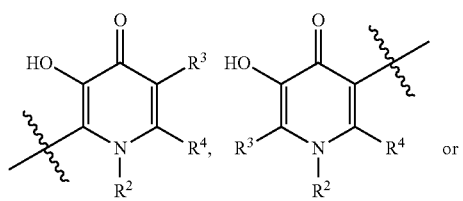

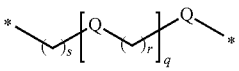

wherein R, R$^2$, R$^3$ and R$^4$ are independently hydrogen or an optionally substituted C$_{1-7}$ alkyl group;
B is a linker group for linking the chelating portion to the reactive group, wherein is represented by the formula:

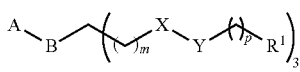

wherein each Q is independently selected from a group consisting of —NR$^5$—, —C(O)NR$^5$—, —C(O)O—, —NR$^5$C(O)NR$^5$—, —NR$^5$C(S)NR$^5$— and —O—, wherein each R$^5$ is independently hydrogen or an optionally substituted C$_{1-7}$ alkyl group, each q and s are independently selected from 0 to 6 and each r is independently selected from 1 to 6;

A is a reactive group for coupling to a biological moiety, a targeting group, a protein, a polypeptide or a delivery vehicle.

The bifunctional conjugate compounds provide a tripodal hexadentate tris(hydroxypyridinone) chelating portion which is able to chelate metallic radionuclides in a very short time (in the order of 5 min or less) and is able to do so at room temperature in water at around physiological pH. The reactive portion is linked to the chelating portion and allows the bifunctional molecule to be conjugated with a targeting group or other vehicle, such as a polypeptide or other biomolecule, drug or nanoparticle. The quick and low temperature labelling of the chelating group allows the bifunctional molecule to be coupled both to a radionuclide with a short half-life, such as $^{68}$Ga (T½=68 minutes) through the chelating portion and to a temperature sensitive targeting group, such as a polypeptide which may denature at radiolabelling temperatures above body temperature.

The efficiency of the chelating reaction also allows labelling at very low delivery vehicle concentration. In this way, a significant proportion of the delivery vehicle is radiolabelled with the radionuclide and, as a result, leading to a very high specific activity. In this way, the bifunctional molecule provides an excellent precursor for a radiolabelling conjugate.

Preferably the reactive group A is the protein-reactive functional group. The protein reactive group may react with proteins or modified proteins or peptides or other vehicles derivatised for the purpose. Preferably the protein-reactive group is a maleimide group, an aldehyde, an ester, or "click" reagent such as an alkyne, azide, alkene, hydrazine, hydrazine derivative, alkoxyamine, alkoxyamine derivative, aminoxy or thiol group. Maleimide, aldehyde and ester groups efficiently react with peptide thiol- or amine-containing residues (cysteine, lysine) and so a conjugate can easily form. Other bioorthogonal functional groups can be engineered into peptides and proteins for the purpose of conjugating them with alkyne, azide, alkene, hydrazine, aminoxy or thiol groups.

Preferably R¹ is

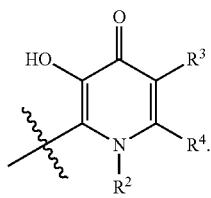

Preferably R², R³ and R⁴ are independently H or CH₃. It is preferred to have relatively small substituents on the heterocyclic ring so that the substituents do not sterically hinder the chelation site of the chelating group and so that the chelator may not become too lipophilic. So in preferred embodiments, R², R³ and R⁴ are H. However, one or more methyl substituents on the heterocyclic group may be used to tailor the solubility and/or the hydrophobicity of the molecule. Accordingly one or more of R², R³ and R⁴ may be CH₃.

Preferably m is 2 or 3. Preferably p is 0 or 1. More preferably when m is 2, p is 1 or when m is 3, p is 0. This gives a tripodal arm length to the chelating group $R_1$ of 5 atoms (m+p=3 plus X and Y). When the tripodal arm length is 5 atoms, the tripodal group is suited to chelating radionuclides, such as gallium.

The linker group B connects the tripodal chelating portion and the reactive functionality (and the e.g. targeting group or carrier vehicle when conjugated). The linking group may be tailored by varying the groups Q, q, r and/or s in order to vary, for example, the length of the linker.

The linker group may be arranged in either direction so that either A or the quaternary carbon (attached to each arm having a chelating group) or both may be attached to Q. In preferred embodiments, B is arranged so that the bifunctional compound is represented by the formula:

The ordering of the atoms in the functional group represented by Q is not limited. In other words, when Q is an amide group, the order of the group from the chelating portion towards the reactive functionality may be —NR⁵— then —C(O)— or vice versa.

Preferably at least one Q is an amide (—C(O)NR⁵—). Preferably q is 1, r is 2 and/or s is 1. More preferably q is 1, r is 2 and s is 1. Preferably R⁵ is hydrogen.

Preferably B is represented by one of the following formulae:

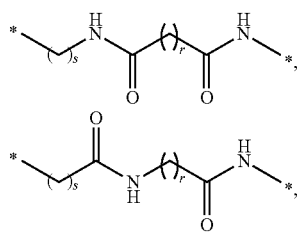

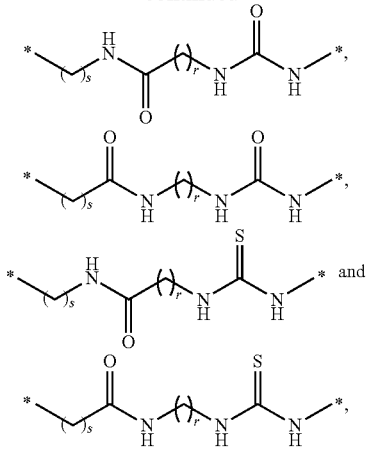

wherein r is selected from 1 to 6 and s selected from 0 to 6. Preferably r is 2 and/or s is 2.

In preferred embodiments, the bifunctional compound is represented by the following formula:

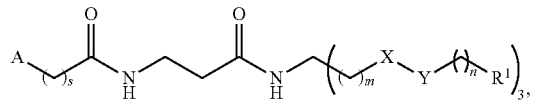

wherein A, s, m, X, Y, n and R¹ are as defined herein.

In preferred embodiments, the radionuclide is an isotope of technetium, rhenium, copper, cobalt, gallium, yttrium, lutetium or other lanthanide, indium, zirconium, scandium. More preferably the radionuclide is Tc-99m, Re-186, Re-188, Co-57, In-111, Cu-60, Cu-61, Cu-62, Cu-64, Cu-67, Tc-94m, Ga-68, Ga-67, Ga-66, Y-90, Y-86, Sc-44, Sc-47, Fe-52, Sn-117m, Tb-149, Gd-153, Ho-166, Lu-177, Zr-89, Bi-213 or Co-55 and more preferably the radionuclide is gallium, and most preferably Ga-68 or Ga-67.

Preferably the targeting group is a member of a specific binding pair that is capable of binding to a binding partner at the target of interest. More preferably the targeting group and target of interest are a receptor and ligand, or an antibody and antigen, or metabolic probe e.g. glucose transporter/glucose, hypoxia/hypoxia responsive moiety, or bone mineral/bisphosphonate, or avidin (or streptavidin or related protein) and biotin (or a biotin-like derivative), or RNA and antisense RNA.

Preferably the targeting group is a peptide, protein, antibody, aptamer or small molecule ligand capable of binding to a binding partner at the target of interest. More preferably the targeting group is a polypeptide capable of binding to phosphatidylserine (PS) so that the bifunctional conjugate composition can be employed in apoptosis or cell death imaging studies. More preferably the targeting group includes Annexin V and the C2 domain of a synaptotagmin, TIMP-2, CEA, RGD peptide, somatostatin receptor targeting peptide, bombesin, gastrin or VCAM targeting peptide.

Preferably the target of interest is an in vivo molecular target. More preferably the target of interest is a ligand or receptor expressed on diseased cells or tissue (of which the abundance or ligand occupancy is to be determined), a cell surface antigen associated with a disease state, tumour markers, such as a cancer specific marker or a tissue specific marker or a marker of a normal process which is up- or down-regulated in a disease state. Preferably the target of interest is a location, an organ, a tissue type or physiological property in a subject undergoing molecular imaging.

Reactive group A may be for coupling to a delivery vehicle. A delivery vehicle as defined herein is a molecular structure for carrying a functional molecule, such as a small molecule drug or toxin with the purpose of delivering the functional molecule for example in a biological system. The functional molecule may be contained within or bonded to a surface of the delivery vehicle. The functional molecule is typically reversibly associated with the delivery vehicle so that the functional molecule may be released at a given location in the biological system. Many such delivery vehicles are known in the art. Preferably the delivery vehicle is a nanoparticle or liposome. Functional molecules, such as pharmaceutical drugs may be bound to the surface of nanoparticles or contained within liposomes.

Thus, when the bifunctional compounds of the present invention are coupled to the delivery vehicle and a radionuclide is chelated by the chelating group $R^1$, the passage of a drug (carried by the delivery vehicle) through a subject may be monitored by imaging of the radionuclide.

The reactive group may (in addition to a biological moiety, a targeting group, a protein, a polypeptide or a delivery vehicle) be for coupling to a secondary imaging label. Preferably the secondary imaging label is an optical label, a paramagnetic label, such as a SPIO, or a quantum dot. More preferably, the imaging label is a paramagnetic label which is a MRI contrast agent with a paramagnetic probe. Alternatively, the imaging label is an optical label which is an organic molecule or metal complex with fluorescent or luminescent properties. The label may, for example in the case of an optical label or paramagnetic label, allow for the bifunctional compound to be used in multi-modal imaging.

The reactive group A may couple with further biological moieties, targeting groups, proteins, polypeptides or delivery vehicles. For example, the bifunctional compound may couple the radionuclide to a targeting group for targeting specific cells in a subject and a liposome containing a pharmaceutical drug. In this way, targeted drug delivery may be monitored during its passage through the biological system.

The method of molecular imaging may include introducing the bifunctional compound (or conjugate thereof) into a biological system (e.g. a subject) either before the radionuclide is introduced into the biological system (i.e. pre-targeting) or after the radionuclide has been chelated to the chelating portion of the bifunctional compound (i.e. pre-assembled).

When the bifunctional compound (or conjugate) is introduced into the biological system before the radionuclide, the bifunctional compound may circulate the biological system to a preferred or targeted location. Then, when the radionuclide is introduced, the radionuclide may quickly pass though the system and chelate with the bifunctional molecule (or conjugate). In this way, the radionuclide may be fixed in a location of interest within a short time of being introduced into the biological system so that the efficacy of the radionuclide is maximised.

When the radionuclide is chelated to the bifunctional compound (or conjugate) before introduction into the biological system, the bifunctional compound may be used to monitor the passage of the bifunctional compound or the conjugate having a biological moiety, a targeting group, a protein, a polypeptide a carrier vehicle or a secondary imaging label attached to the compound through the biological system.

Preferably the biological moiety, targeting group, protein, polypeptide or delivery vehicle are bound to the bifunctional compound to form a bifunctional compound conjugate before introduction of the bifunctional compound composition into the biological system or subject.

Preferably the biological system is a subject undergoing diagnosis or therapy for a disease or condition. The therapy may be radionuclide therapy. In particular the therapy may be cancer treatment using the radionuclide or a chemotherapeutic agent associated with the bifunctional molecule, for example via the delivery vehicle to which it is attached. Preferably the bifunctional molecule is associated with or bound to a therapeutic agent. Alternatively, the subject may be a subject in whom the biodistribution of the targeting molecule or delivery vehicle is being evaluated.

In a second aspect, the present invention provides a bifunctional compound conjugate for chelating a radionuclide for use in molecular imaging, wherein the conjugate is represented by the formula:

or salts thereof;
wherein one of X and Y is C=O and the other is NR;
wherein m and p are independently 0 to 6;
wherein $R^1$ is a chelating group selected from:

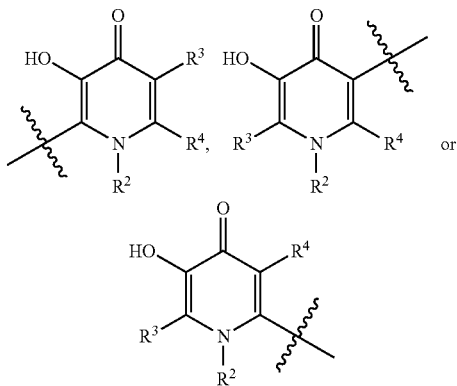

wherein R, $R^2$, $R^3$ and $R^4$ are independently hydrogen or an optionally substituted $C_{1-7}$ alkyl group;
B is a linker group for linking the chelating portion to the reactive group, wherein is represented by the formula:

wherein each Q is independently selected from a group consisting of —$NR^5$—, —C(O)$NR^5$—, —C(O)O—, —$NR^5$C(O)$NR^5$—, —$NR^5$C(S)$NR^5$—, —O—, wherein each $R^5$ is independently hydrogen or an optionally substituted $C_{1-7}$ alkyl group, each q and s are independently selected from 0 to 6 and each r is independently selected from 1 to 6; and
A* is a reacted reactive group for coupling to T, wherein T is a biological moiety, a targeting group, a protein, a polypeptide or a delivery vehicle.

In a further aspect, the present invention provides a kit for use in a method of molecular imaging or therapy comprising: a bifunctional molecule composition having a bifunctional compound as described herein, wherein the compound is linked to a biological moiety, a targeting group, a protein, a polypeptide or a delivery vehicle through reactive group A; and an imaging composition comprising a radionuclide as described herein.

In another aspect, the present invention provides a kit for use in a method of molecular imaging or therapy comprising: a bifunctional molecule composition having a bifunctional compound as described herein; and a biological moiety, a targeting group, a protein, a polypeptide or a delivery vehicle for coupling to the bifunctional molecule. The kit may also include an imaging composition comprising a radionuclide as described herein.

In another aspect, the present invention provides a method of molecular imaging a target of interest in a biological system, the method comprising:
  (a) administering to a subject a composition comprising bifunctional compound as described herein, wherein the compound is linked to a biological moiety, a targeting group, a protein, a polypeptide or a delivery vehicle through reactive group A;
  (b) administering to the subject an imaging composition comprising a radionuclide, wherein the chelating group $R^1$ of the bifunctional compound is capable of chelating the radionuclide; and
  (c) detecting the radionuclide to image the target of interest in the biological system.

In another aspect, the invention provides a method of molecular imaging a target of interest or passage of interest in a biological system, the method comprising:
  (a) chelating a radionuclide to the bifunctional molecule through the chelating group as described herein, wherein the compound is linked to a biological moiety, a targeting group, a protein, a polypeptide or a delivery vehicle through reactive group A, to form a radiolabelled bifunctional molecule compound;
  b) administering to a subject a composition comprising the radiolabelled bifunctional compound; and
  (c) detecting the radionuclide to image the target or passage of interest in the biological system.

Preferably the radionuclide is a radionuclide capable of delivering radiotherapy to the target of interest. Preferably the radionuclide is Cu-67, Re-186, Re-188, Y-90, Lu-177, Sc-47 or Bi-213.

The preferred and optional features of any one aspect may be applied to any other aspect. In particular, the preferred features of the bifunctional compounds apply to the method of molecular imaging and vice versa.

Embodiments of the present invention will now be described by way of example and not limitation with reference to the accompanying figures.

BRIEF DESCRIPTION OF THE FIGURES

FIG. 11A (left): PET/CT scan (maximum intensity projection) of a mouse from group 3 showing pre-targeting using CP256-SER4: 8 week-old C57Bl/6 injected with CP256-SER4 followed by Ga-68 acetate, showing liver/spleen uptake. Image taken at 1.5 h post injection. FIG. 11B (right): for comparison, mouse injected with Ga-68 acetate only, showing retention in blood pool and accumulation in joints.

DETAILED DESCRIPTION

A: Targeting the Site of Interest

Figure 1:
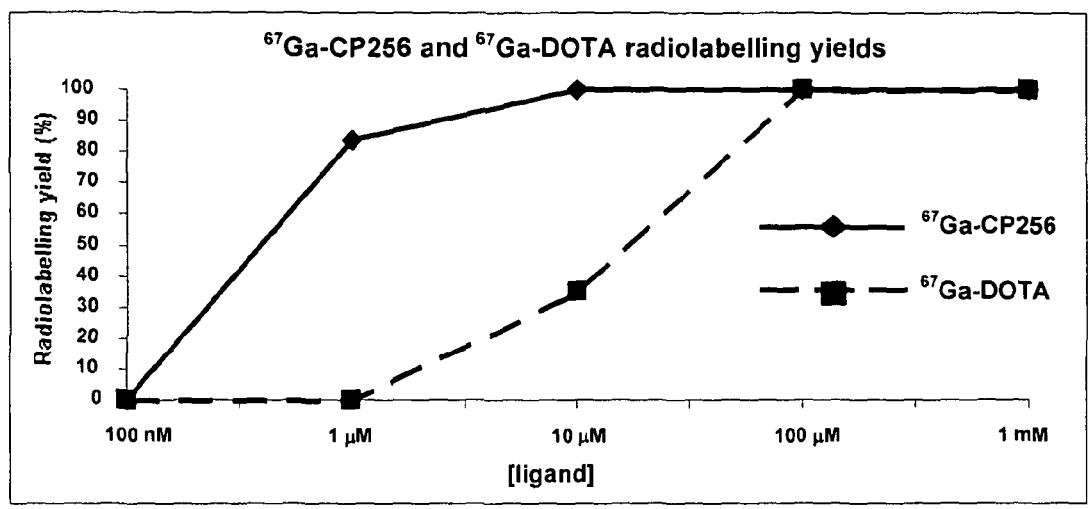
FIG. 1. shows the radiolabelling yield of chelating portion CP256 with $^{67}$Ga after 5 minutes at room temperature compared to the radiolabelling yield of DOTA with $^{67}$Ga after 40 minutes at 80° C.

Where the bifunctional compound is for coupling to a targeting molecule, a wide range of primary targeting groups may be linked to the bifunctional compounds to direct the bifunctional compounds with the chelating group to different targets of interest in the biological system in question.

In one aspect, the target of interest will comprise a member of a specific binding pair that is capable of specifically binding to the primary targeting group in the system, such that they will be members of a pair of molecules which have particular specificity for each other and which in normal conditions bind to each other in preference to binding to other molecules. Examples of specific binding pairs are well known in the art and include for example receptors and ligands, enzymes and substrates, antibodies and antigens. Thus, primary targeting groups may be peptides, proteins or other biological molecules, such as aptamers, or small molecule ligands, that bind to specific in vivo molecular targets. Classes of targets of interest include ligands or receptors or transporters expressed on diseased cells or tissue, cell surface antigen associated with disease states, or tumour markers, e.g. cancer specific markers or tissue specific markers.

One group of primary targeting groups are polypeptides capable of binding to phosphatidylserine (PS) so that the bifunctional molecule conjugates of the present invention can be employed in apoptosis or cell death imaging studies. Examples of such polypeptides include Annexin V and the C2 domain of a synaptotagmin. Polypeptides that comprise one or more C2 domains are well known in the art. While some polypeptides have only one C2 domain, others have two or more C2 domains, and the domains are generally described by attaching a letter (in alphabetical order) to the end of the name (e.g., C2A, C2B, and so on). For a protein that contains only one C2 domain, the domain is simply referred to as C2 domain. While the examples below use the C2A domain of rat synaptotagmin I, other C2 domains that are capable of binding to PS could be employed instead, for example a C2A domain of a synaptotagmin of another species. Further examples of proteins that contain a C2 domain include but are not limited to synaptotagmin 1-13, protein kinase C family members of serine/threonine kinases, phospholipase A2, phospholipase δ1, cofactors in the coagulation cascade including factors V and VIII, and members of the copine family. Human synaptotagmins include synaptotagmin 1-7, 12 and 13.

Other proteins that may be employed in the present invention include polypeptides capable of specifically binding to markers that are expressed by cancer cells, thereby enabling the cancer cells to be imaged using the bioconjugates. By way of example, the present invention can employ an anti-CD33 antibody, or fragment thereof, for imaging cancer cells expressing CD33 such as cells of myelomonocytic lineage and leukaemic cells, see Emberson et al., J. Immunol. Methods. 305(2):135-51, 2005. A further example is the use of a tissue inhibitor of metalloproteinases (TIMPs), such as TIMP-2, for imaging matrix metalloproteinase expression, as expression of metalloproteinases has been implicated in metastatic processes, see Giersing et al., Bioconjug Chem. 12(6): 964-71, 2001. A further example of a polypeptide that can be used to make conjugates according to the present invention is complement receptor 2 (CR2). Antibodies capable of binding to the glycoprotein carcinoembryonic antigen (CEA) may also be used as primary targeting groups as members of this family of glycoproteins are expressed on colorectal cancer cells, gastric cancer cells, pancreatic cancer cells, lung cancer cells, medullary thyroid cancer cells and breast cancer cells.

A further example may exploit the affinity or the peptide sequence arginine-glycine-aspartic acid (RGD) for the $\alpha_v\beta_3$ integrin expressed highly in the endothelium of tissues undergoing angiogenesis as is commonly seen in tumours, atherosclerotic plaque and repairing diseased tissue such as infarcted myocardium, by linking an RGD peptide derivative to the bifunctional compound by means of a suitable reactive group A.

A further example may exploit the affinity of the peptide octreotide or other related analogue of somatostatin, which may bind to the somatostatin receptor expressed highly at the surface of cancer cells e.g. in carcinoid, medullary thyroid carcinoma and other neuroendocrine tumours, by linking a somatostatin analogue peptide to the bifunctional compound by means of a suitable reactive group A.

Another example may exploit the affinity of antibodies to cell adhesion molecules. One example is the affinity of the monoclonal antibody, SER 4, to the macrophage adhesion molecule, sialoadhesin. Sialoadhesin is found on the surface of macrophages, and, for example, in high amounts on macrophages of the spleen, liver, lymph node, bone marrow colon and lungs.

The skilled person will be able to use other targeting groups such as bombesin, gastrin, or VCAM targeting peptide.

Preferably, the primary targeting group may be linked to the bifunctional compound as a conjugate having a functional group for binding to the bifunctional compound and the reactive group for linking to the primary targeting group. Various possibilities for achieving this will be apparent to the skilled person. By way of example, in one embodiment, a reactive group for site-specific linkage to the primary targeting group may be employed, for example a maleimide group for site-specific linkage to thiol groups in a biomolecule such as a peptide, polypeptide or antibody. The maleimide group can then be site-specifically linked to a thiol group, for example of a cysteine residue incorporated site-specifically into the peptide or protein for the purpose. In another example the reactive group in the bifunctional chelator would be an aldehyde or ketone group able to react site-specifically with a protein or peptide to which a hydrazine or similarly reactive group has been site-specifically incorporated (e.g. using a hydrazinonicotinic acid derivative) to form a hydrazone or similar link.

In some cases, the primary targeting group may comprise a suitable polypeptide or protein, or a fragment or domain thereof. Accordingly, while for convenience the methods herein are generally described by reference to "polypeptides", this should be taken to include shorter sequences of amino acids (e.g., from 3 to 10 amino acids in length to 30, 40 or 50 amino acids in length), sometimes referred to in the art as peptides. The term should also be taken to include polypeptides having secondary, tertiary or quaternary structure, generally referred to as proteins, as well as multidomain proteins. In some embodiments, and in the examples provided below, the polypeptides used as primary targeting groups are protein domains. "Protein domains" are fragments of a full length protein that have the ability to retain structure independent of the full length protein, typically forming a stable and folded three-dimensional structure. Many proteins consist of several structural protein domains and it is common for a particular domain to be found in a range of related proteins. Protein domains vary in length from between about 25 amino acids up to 500 amino acids in length, or from 50 amino acids to 250 amino acids, or from 75 amino acids to 150 amino acids.

In the present invention, where the polypeptide is an antibody, this term describes an immunoglobulin whether natural or partly or wholly synthetically produced. The term also covers any polypeptide or protein comprising the antigen binding domain of an antibody; antibody fragments which comprise an antigen binding domain such as Fab, scFv, Fv, dAb, Fd; and diabodies. It is possible to take monoclonal and other antibodies and use techniques of recombinant DNA technology to produce other antibodies or chimeric molecules which retain the specificity of the original antibody. Such techniques may involve introducing DNA encoding the immunoglobulin variable region, or the complementarity determining regions (CDRs), of an antibody to the constant regions, or constant regions plus framework regions, of a different immunoglobulin. See, for instance, EP 0 184 187 A, GB 2,188,638 A or EP 0 239 400 A.

Antibodies can be modified in a number of ways and the term "antibody molecule" should be construed as covering any specific binding member or substance having an antibody antigen-binding domain with the required specificity. Thus, this term covers antibody fragments and derivatives, including any polypeptide comprising an immunoglobulin binding domain, whether natural or wholly or partially synthetic. Chimeric molecules comprising an immunoglobulin binding domain, or equivalent, fused to another polypeptide are therefore included. Cloning and expression of chimeric antibodies are described in EP 0 120 694 A and EP 0 125 023A. It has been shown that fragments of a whole antibody can perform the function of binding antigens. Examples of binding fragments are (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment (Ward, E. S. et al., Nature 341, 544-546 (1989)) which consists of a VH domain; (v) isolated CDR regions; (vi) F(ab')2 fragments, a bivalent fragment comprising two linked Fab fragments (vii) single chain Fv molecules (scFv), wherein a VH domain and a VL domain are linked by a peptide linker which allows the two domains to associate to form an antigen binding site (Bird et al, Science, 242; 423-426, 1988; Huston et al, PNAS USA, 85: 5879-5883, 1988); (viii) bispecific single chain Fv dimers (PCT/US92/09965) and (ix) "diabodies", multivalent or multispecific fragments constructed by gene fusion (WO 94/13804; Holliger et al, P.N.A.S. USA, 90: 6444-6448, 1993). Fv, scFv or diabody molecules may be stabilised by the incorporation of disulphide bridges linking the VH and VL domains (Reiter et al, Nature Biotech, 14: 1239-1245, 1996). Minibodies comprising a scFv joined to a CH3 domain may also be made (Hu et al, Cancer Res., 56: 3055-3061, 1996).

Affibodies may also be used as a primary targeting group. Affibodies are small high affinity proteins that may bind specifically to a large number of target proteins or peptides. Affibodies imitate monoclonal antibodies in many respects and are classed as antibody mimetics. The selection of affibody should not be limited and many affibodies are known in the art, such as unconjugated anti-TNF-α affibody. Anti-TNF-α affibody may be produced in E. coli and targets human cytokine tumor necrosis factor α, TNF-α. TNF-α is a pleiotropic inflammatory cytokine. The cytokine is produced by several types of cells, but especially by macrophage. It acts as a key mediary in the local inflammatory immune response and has further immune regulatory functions. TNF-α is an acute phase protein which initiates a cascade of cytokines and increases vascular permeability, thereby recruiting macrophage and neutrophils to a site of infection. Therefore, TNF-α is an important target for inflammation in atherosclerotic lesions and inflammations.

Each bifunctional compound may be linked to a plurality of primary targeting groups, thereby increasing (a) the affinity of the primary targeting groups for the target of interest as the overall affinity increases as the product of the affinity of each targeting group for the target and/or (b) the rate of binding to the target, i.e. the likelihood of binding ensuing from each encounter between target and primary targeting group in vivo.

B: Imaging Probes

The imaging probes that are capable of binding to the bifunctional compounds comprise a radionuclide (bound through the chelating group).

The imaging probes (metallic radioisotopes) used in accordance with the present invention have the property of binding to the chelating portion of the bifunctional compounds either in vitro or in vivo, in either the pre-targeted or pre-assembled approaches. One possibility for achieving this is to use radionuclides that have an intrinsic binding affinity for chelating portion of the bifunctional compounds. By way of example, $^{68}Ga^{3+}$ is capable of binding to the hydroxypyridinone groups of the chelating portion and can be used in PET imaging techniques.

The radionuclide probes used in accordance with the present invention may use a range of different radionuclides depending on the application for which the probes are intended. Examples of radionuclides that may form part of the probes of the present invention include radionuclides of technetium, rhenium, copper, cobalt, gallium, yttrium, lutetium, indium, zirconium, scandium, namely Tc-99m, Ga-67, In-111 (SPET), Cu-64, Cu-60, Cu-61, Cu-62, Tc-94m, Ga-68, Co-55, Zr-89, Sc-44 (PET), Cu-67, Re-186, Re-188, Y-90, Lu-177, Sc-47 or Bi-213 (radionuclide therapy). The present invention may employ the radionuclides alone or in combinations.

The radionuclide may be in any form, such as a solvate, hydrate, salt or weak chelate. Solvates, hydrates, salts and weak chelates of radionuclides are known in the art. When the radionuclide is to be administered to a subject in a radionuclide composition (for example, when the bifunctional compound chelates the radionuclide in the subject after administration), the radionuclide should be in a pharmaceutically acceptable form. For example, the radionuclide may be a citrate or acetate salt of the metal ion.

The present invention may also involve the use of secondary imaging labels, such as an optical label or a paramagnetic label (through the reactive group A) that may be linked to or associated with the bifunctional compounds, for example to enable multi-modal imaging to be carried out. Examples of optical probes include fluorophores such as fluorescein and luminescent molecules and complexes such as lanthanide complexes and tricarbonylrhenium-quinolinate conjugates. The possibility to incorporate optical probes as well as radionuclides and MR contrast agents provides the opportunity to combine modalities to enhance diagnosis and detection, for example the location of disease at the whole body level can be identified by whole body scanning with PET or SPECT while the same tracer may be detected visually during surgery to assist identification of diseased tissue. Similarly, combined PET and MR imaging can provide the advantage of high sensitivity (PET, SPET), quantification of signal (PET) and anatomical resolution (MR) and measurement of the microenvironment (MR contrast enhancement).

C: Conjugation Chemistry

The bifunctional compounds of the present invention may use a range of different chemistries and techniques for linking the biological moiety, targeting group, label, protein or polypeptide to the bifunctional compounds and/or for introducing further groups and properties into the bifunctional compounds of the present invention.

Thus, in the present invention, the reactive group provides a way of coupling the targeting group to the bifunctional compound, for example when the reactive group is a maleimide group (to bind to the thiol side chain of cysteine in the protein/peptide sequence)

Uses of the Present Invention

The bifunctional compounds of the present invention may be used for the molecular imaging of diseases, such as cancer, cardiovascular disease, immunological disease and associated conditions, such as transplant, inflammation, leukocyte tracking, stem cell tracking, allergy and infection. The bifunctional compounds may also be employed for radionuclide therapy for treating cancer and arthritis.

The applications of the bifunctional compounds and radionuclides of the present invention include a wide range of imaging and spectroscopic applications that can employ the radionuclide and/or a further label, for example, in multi-modal imaging studies. As described herein, the bifunctional compounds are particularly useful for in vivo imaging applications such as cell death imaging, for example using bifunctional compounds for the detection of apoptosis. This might be useful in a number of different medical or research applications, for example in the fields of oncology (e.g. in monitoring response to chemotherapy), cardiovascular medicine (e.g. in imaging damaged myocardium post myocardial infarction) or graft rejection (e.g. in imaging cardiac allograft rejection).

The present invention is particularly relevant to nuclear medicine imaging techniques, such as Single Photon Emission Tomography (SPET), an imaging technique that detects gamma rays emitted from a radionuclide to produce a three dimensional image of the distribution of the radionuclide in a sample or subject, and Positron Emission Tomography (PET), an imaging technique that provides three-dimensional images by detecting pairs of gamma rays emitted indirectly by a positron-emitting radionuclide introduced into a sample or subject. By way of example SPET studies can be carried out using In-111 and PET studies using Ga-68. The skilled person, however, will be aware of other suitable SPET and PET radionuclides that can be employed in the present invention. Generally, the present invention may be employed for positron emission tomography (PET), single photon emission tomography (SPET), optical (OI) and/or magnetic resonance imaging (MRI) by appropriate selection of imaging probe, or for radionuclide therapy by selection of the appropriate radionuclide (e.g. Y-90, Lu-177).

The bifunctional compounds of the present invention may be used in methods of multi-modal imaging, that is where information or images are derived from two different techniques, either by the detection of the imaging probe capable of detection using two different techniques or by providing a second label at the site in the biological system where the bifunctional compounds become localised, most conveniently by linking or associating the second label with the bifunctional compounds as explained in detail above. Multimodal studies will be co-registered and may entail simultaneous imaging with two modalities or may need to take place in two steps, but generally employ the same sample so that spatial information obtained using the two techniques can be compared. Examples of multi-modal imaging include PET/CT, SPET/CT, PET/MR and SPET/MR

EXAMPLES

Example 1

Synthesis of Chelator CP256 (Compound 52)

The tris tert-butyl esters 61 and 62 were synthesised by following established literature methods (G. R. Newkome, R. K. Behera, C. N. Moorefield and G. R. Baker, *J Org Chem*, 1991, 56, 7162-7167).

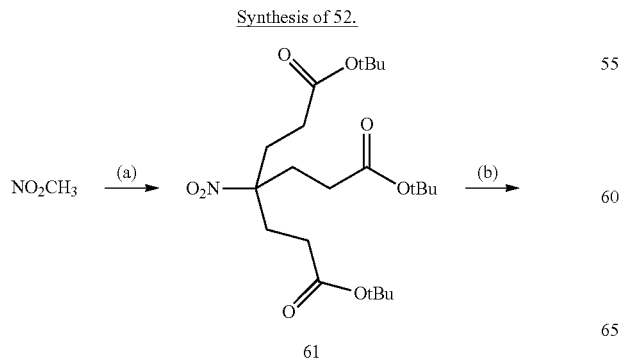

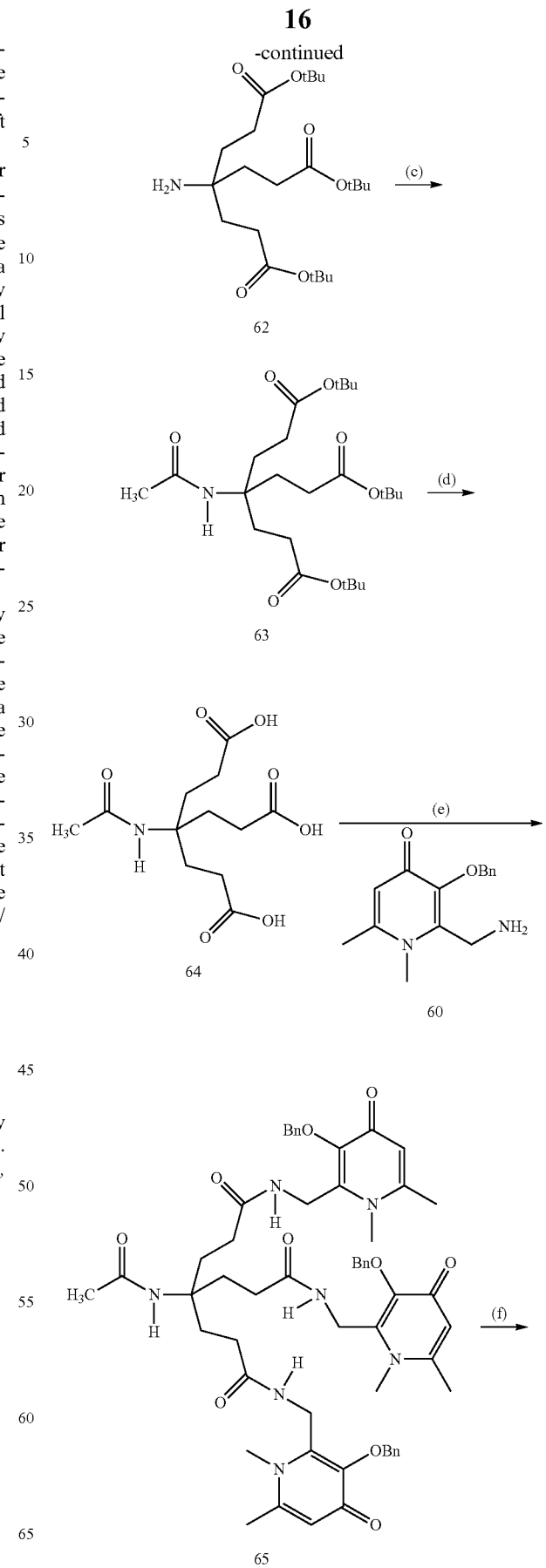

-continued

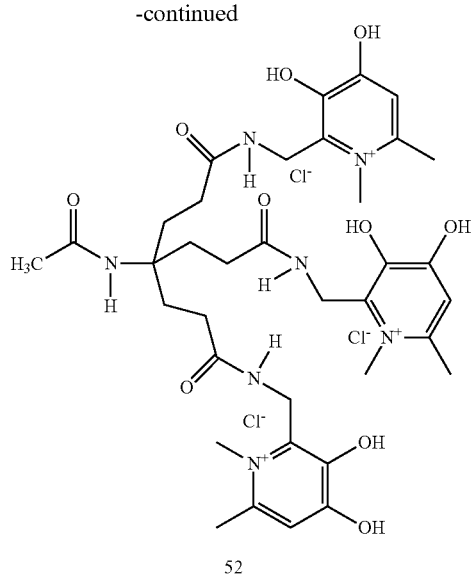

52

Materials and methods: (a) Triton B, Tert-butyl acrylate, DME, 70° C.; (b) T-1 Raney Ni, H₂, 25° C., EtOH; (c) CH₃COCl, Et₃N, CH₂Cl₂, 0-25° C., (d) HCOOH; (e) 60, DCCI, HoBt, DMF 25° C.; (f) Pd/C, H₂, HCl, CH₃OH, 25° C.

Nitro tripod 61 was produced by the reaction of nitromethane and tert-butyl acrylate in the presence of benzyltrimethylammonium hydroxide and recrystallised from ethanol in 57% yield. The nitro group of 61 was then reduced to an amine to form 62 by hydrogenation with a T-1 Raney Nickel catalyst,[5] which was specially prepared from a nickel/aluminium alloy. Acetylation of 62 with acetyl chloride and purification by column chromatography gave 63 in 72% yield. The tert-butyl groups were then removed with formic acid and the product, compound 64 was recrystallised from ethanol/petroleum spirit with a yield of 93%.

The conjugation of the bidentate moieties to the tripodal framework and subsequent deprotection to create 52 is shown schematically above. 1 equivalent of tri-acid 64 was reacted with 3.6 equivalents of bidentate compound 60 in a coupling reaction with DCCI and HOBt in DMF. After removal of the solvent, the protected hexadentate ligand 65 was purified by column chromatography in 50% yield. The benzyl protecting groups were removed by catalytic hydrogenation (Pd/C) in an acidic solution (HCl) of methanol. After removal of the catalyst, the tris HCl salt of 52 was precipitated from methanol/diethylether and dried under vacuum, resulting in 0.4 g (74%) of 52 as a white solid.

Experimental Details

All chemicals were purchased from Sigma Aldrich and Acros Organics and were reagent grade or better. Solvents were purchased from Fisher Scientific, Sigma Aldrich and VWR. NMR solvents were purchased from GOSS Scientific and NMR tubes were manufactured by Wilmad. TLC plates (silica gel 60 UV₂₅₄ on alumina backing) and silica gel for column chromatography were purchased from Merck.

Samples were dried in a vacuum oven (Gallenkamp, rated to ≤250° C.) connected to a vacuum pump (BOC-Edwards.) Samples were hydrogenated on a Parr hydrogenator (room temperature) at 40 psi with automatic shaking. Infrared Spectra were acquired on a Perkin Elmer Spectrum one FTIR using KBr disks. The software used was called "Spectrum."

¹H-NMR spectra were acquired on a 400 MHz Ultra-shield magnet (Bruker) and with XWin-NMR software. Spectra were analysed on MestReNova software version 5.3 (Mestrelab Research.) Mass spectrometry samples were submitted to the EPSRC Mass Spectrometry Centre, Swansea or the Mass Spectrometry facility, King's College, London. Samples at EPSRC were run on a Waters ZQ4000 quadrupole mass spectrometer (ESI), a Finnigan MAT 95 XP high resolution double focusing mass spectrometer (EI, CI) or a Micromass Quattro II quadrupole mass spectrometer (EI.) Samples at King's College were run on a Thermofisher LCQ DECA XP ion trap mass spectrometer.

Isotopic distributions were calculated using Molecular Weight Calculator version 6.46. The resulting graph data were extracted and processed in Microsoft Excel 2003.

2-Chloromethyl-5-hydroxypyran-4(1H)-one (Chlorokojic acid) (54)

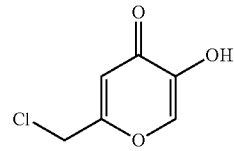

50 g kojic acid (350 mmol, 1 equiv) was added to 220 ml thionyl chloride with stirring. The reaction vessel was cooled with ice and the mixture was stirred for 1 hour until a bright yellow suspension had formed. The mixture was vacuum filtered to give a crude white solid after washing with petroleum spirit. This solid was recrystallised from hot water to give 40 g of off-white crystals in 71% yield.

¹H NMR (DMSO-d₆) σ 9.2 (s, 1H 3-OH) 8.1 (s, 1H 2-H) 6.5 (s, 1H 5-H) 4.6 (s, 2H 6-CH₂—Cl)

2-Methyl-5-hydroxypyran-4(1H)-one (Allomaltol) (55)

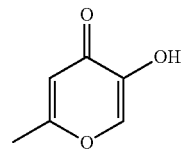

20 g chlorokojic acid (54) (125 mmol, 1 equiv) was added to 100 ml distilled water and stirred at 50° C. Zinc dust (17 g) was slowly added to the solution and the temperature was increased to 70° C. 40 ml of concentrated HCl was added dropwise into the stirring mixture slowly over a period of 90 minutes. During this time, the chlorokojic acid dissolved. After stirring for a further 3 hours at 70-80° C., the now dark brown solution was hot-filtered to remove any solids. After cooling, the product was extracted with 5×70 ml portions of CH₂Cl₂. The solution was dried (Na₂SO₄) and the solvent was removed in vacuo. The crude solid was recrystallised from hot isopropanol, resulting in 8.63 g of beige crystals in 55% yield.

¹H NMR (DMSO-d₆) σ 9.0 (s, 1H 2-H) 8.0 (s, 1H 3-OH) 6.2 (s, 1H 5-H) 2.2 (s, 3H 6-CH₃)

2-Hydroxymethyl-3-hydroxy-6-methyl-pyran-4(1H)-one (56)

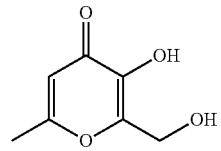

3 g allomaltol (55) (23.8 mmol, 1 equiv) was added to a stirred solution of 1.05 g NaOH in 25 ml distilled water. 2.2 ml of a 37% solution of formaldehyde was added dropwise over 10 minutes. The solution was stirred for a further 18 hours at room temperature. The pH was adjusted to 1 with concentrated HCl at which point a white precipitate formed. To allow complete precipitation, the solution was cooled at 4° C. for 24 hours. The solid was filtered and washed with cold diethyl ether and dried in vacuo resulting in 2.92 g of a white solid in 78% yield.

$^1$H NMR (DMSO-$d_6$) σ 8.8 (s, 1H 3-OH) 6.2 (s, 1H 5-H) 4.3 (s, 2H 2-CH$_2$—OH) 2.2 (s, 3H 6-CH$_3$)

2-Hydroxymethyl-3-benzylroxy-6-methyl-pyran-4(1H)-one (57)

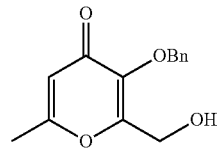

To 60 ml of CH$_3$OH was added 10 g of 56 (64 mmol, 1 equiv) and the solution was heated to reflux. A solution of 2.82 g NaOH (70 mmol, 1.1 equiv) in 6 ml H$_2$O was added slowly to the refluxing solution. 12.05 g benzyl bromide (70 mmol, 1.1 equiv) was dropped slowly into the refluxing solution over 30 minutes. The solution was refluxed for a further 16 hours. The solvent was removed in vacuo and the residue taken up into 180 ml CH$_2$Cl$_2$. The insoluble NaBr was filtered off. The organic layer was washed with two 100 ml portions of 5% aqueous NaOH and then with 2×100 ml portions of water, dried (Na$_2$SO$_4$) and evaporated to leave a clear yellow oil. The oil was recrystallised from CH$_2$Cl$_2$ and petroleum spirit to give 9.8 g of a white solid in 62% yield.

m/z 247 (M+H)$^+$ [ES$^+$]
$^1$H NMR (CDCl$_3$) σ 7.25 (m, 5H 3-O—CH$_2$-Bnz) 6.1 (s, 1H 5-H) 5.1 (s, 2H 3-O—CH$_2$-Bnz) 4.2 (m, 2H 2-CH$_2$—OH) 2.15 (s, 3H 6-CH$_3$)

1,6-Dimethyl-2-hydroxymethyl-3-benzyloxypyridin-4(1H)-one (58)

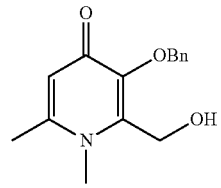 [SMILES: Cc1cc(=O)c(OCc2ccccc2)c(CO)n1C]

4.92 g 57 (20 mmol, 1 equiv) was added to 60 ml CH$_2$Cl$_2$ with stirring. 3.4 g 3,4-dihydro-2-H-pyran (42.5 mmol, 2.2 equiv) was added followed by 60 mg p-toluenesulphonic acid as a catalyst.

After stirring for 3 hours the mixture was added to a separating funnel and washed with 2×40 ml Na$_2$CO$_3$ (5%) followed by 2×40 ml distilled water. The organic layer was dried (Na$_2$SO$_4$) and evaporated to give a yellow oil, which was redissolved in 20 ml EtOH. 200 ml NH$_2$CH$_3$ (40%, aqueous) was added and the mixture stirred at 70° C. for 18 hours. The solvent was removed in vacuo and the resulting oil was redissolved in 40 ml EtOH. 2 ml concentrated HCl (37%) was added and the solution was refluxed for 4 hours. The solvent was removed in vacuo and 100 ml distilled water was added to the residue. The solution was washed with 2×50 ml diethylether. The pH of the aqueous phase was then adjusted to 9 with 10 N aqueous NaOH. The solution was added to a separating funnel and extracted with 4×100 ml CH$_2$Cl$_2$. The organic layer was dried with anhydrous Na$_2$SO$_4$ and the solvent was removed to give a crude brown solid, which was recrystallised from CH$_3$OH and diethyl ether to give 2.8 g of white crystals in 54% yield.

m/z 260 (M+H)$^+$ [ES$^+$]
$^1$H NMR (DMSO) σ 7.3-7.5 (m, 5H 3-O—CH$_2$-Bnz) 6.15 (s, 1H 5-H) 5.4 (m, 1H 2-CH$_2$—OH) 5.0 (s, 2H 3-O—CH$_2$-Bnz) 4.5 (m, 2H 2-CH$_2$—OH) 3.58 (s, 3H 6-CH$_3$) 2.28 (s, 3H 1-N—CH$_3$)

1,6-Dimethyl-2-phthalimidomethyl-3-benzyloxypyridin-4(1H)-one (59)

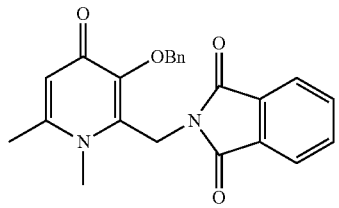 [SMILES: Cc1cc(=O)c(OCc2ccccc2)c(CN2C(=O)c3ccccc3C2=O)n1C]

8.6 g triphenylphosphine (32 mmol, 1.2 equiv) and 4.8 g phthalimide (32 mmol, 1.2 equiv) were added to a stirred suspension of 58 (7 g, 27 mmol, 1 equiv) in 150 ml THF at 0° C. 6.47 g Diisopropyl azodicarboxylate [DIAD] (32 mmol, 1.2 equiv) was added dropwise over 30 minutes. The solution was allowed to warm to room temperature and was stirred for a further 17 hours, after which time the solution was filtered. The solid was washed with cold THF to give 9.92 g of a white amorphous solid in 95% yield.

$^1$H NMR (CDCl$_3$) σ 7.65 (m, 4H 2-CH$_2$-Phthalimide) 7.15 (m, 5H 3-O—CH$_2$-Bnz) 6.25 (s, 1H 5-H) 5.35 (s, 2H 3-O—CH$_2$-Bnz) 4.75 (s, 2H 2-CH$_2$-Phthalimide) 3.5 (s, 3H 1-N—CH$_3$) 2.1 (s, 3H 6-CH$_3$)

1,6-Dimethyl-2-aminomethyl-3-benzyloxypyridin-4(1H)-one (60)

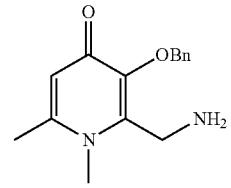 [SMILES: Cc1cc(=O)c(OCc2ccccc2)c(CN)n1C]

10 g of 59 (26 mmol, 1 equiv) was dissolved in 100 ml EtOH. 17 ml N$_2$H$_4$ (5.5% aqueous) was added and the solution was refluxed for 3 hours. 59 did not fully dissolve until refluxing had begun. The solution was allowed to cool, at which point it solidified. Water was added and the pH adjusted to 1 with conc. HCl. After overnight cooling at 4° C., the solution was filtered. The pH of the filtrate was adjusted to 14 with 10 N NaOH and extracted with 5×100 ml CH$_2$Cl$_2$. The extracts were combined and dried over Na$_2$SO$_4$. The solvent was removed in vacuo to give 6.2 g of a white solid in 92% yield.

m/z 259 (M+H)+ [ES+]

¹H NMR (CDCl₃) σ 7.25 (m, 5H 3-O—CH₂-Bnz) 6.35 (s, 1H 5-H) 5.25 (s, 2H 3-O—CH₂-Bnz) 3.7 (s, 2H 2-CH₂—NH₂) 3.6 (s, 3H 1-N—CH₃) 2.3 (s, 3H 6-CH₃)

Di-tert-butyl 4-Nitro-4-[2-(tert-butoxycarbonyl)ethyl]-heptanedioate (61)

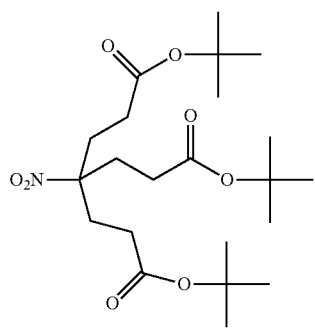

1.53 g nitromethane (25 mmol, 1 equiv) was added to 10 ml 1,2-dimethoxyethane (DME.) 0.25 ml of benzyltrimethylammonium hydroxide (Triton B) was added and the solution heated to 70° C. 9.93 g Tert-butyl acrylate (77.5 mmol, 3.1 equiv) was added in 1 ml portions along with another 2×0.25 ml portions of Triton B to keep the temperature between 70-80° C. Following complete addition of the reagents, the solution was heated at 70° C. for a further hour. The solvent was removed in vacuo and the residue redissolved in 60 ml CHCl₃ and placed in a separating funnel. The organic layer was washed with 20 ml HCl (10% aqueous) followed by 3×20 ml conc. NaCl solution. The organic layer was dried with Na₂SO₄, filtered and the solvent was removed in vacuo. The crude product was recrystallised from hot EtOH, filtered and washed with ice cold EtOH to give 6.4 g of white crystals in 57% yield.

m/z 463 (M+NH₄)+ [CI]

¹H NMR (CDCl₃) σ 2.2 (s, 12H [CH₂—CH₂—COO-tbu]₃) 1.45 (s, 27H [CH₂—CH₂—COO-tbu]₃)

IR (KBr) 2975s (CH₂), 1723s (C=O), 1536s (NO₂) cm⁻¹

T-1 Raney Nickel Catalyst

To a 1 L three necked round bottomed flask was added 600 ml of a 10% solution of NaOH followed by 40 g of Nickel-Aluminium alloy. The solution was stirred with a magnetic stirrer bar and heated at a temperature of 90-95° C. After 40 minutes of heating the nickel began to adhere to the magnetic stirrer, impeding the stirring process. At this point stirring was continued manually with a glass rod. Heating was discontinued after one hour and the nickel was left to settle. Once the Nickel catalyst had settled and the solution had cooled, the supernatant was decanted and discarded. The catalyst was washed with 3×200 ml distilled water and 5×50 ml ethanol. Care was taken to ensure that the catalyst was covered with liquid and not exposed to the air during the washing steps. The catalyst was then stored in a refrigerator at 4° C. under 50 ml ethanol.

Di-tert-butyl 4-Amino-4-[2-(tert-butoxycarbonyl)ethyl]-heptanedioate (62)

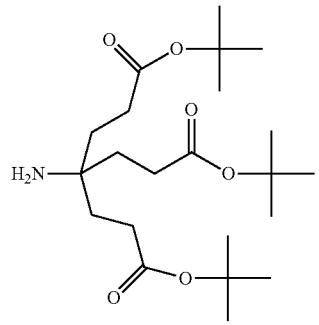 [SMILES: CC(C)(C)OC(=O)CCC(CCC(=O)OC(C)(C)C)(CCC(=O)OC(C)(C)C)[N+](=O)[O-]]

5 g of 61 (11.24 mmol, 1 equiv) was dissolved in 100 ml EtOH. 4 g of T-1 Raney Nickel catalyst was added. The solution was hydrogenated at 40 psi (room temperature) for 7 days. During this period, the H₂ pressure was maintained at 40 psi, and the reaction stopped once the pressure ceased to reduce any further. 61 did not fully dissolve at first but did during the period of hydrogenation. The solution was filtered through celite and the solvent was removed in vacuo to give 4.5 g of an oil in quantitative yield, which solidified upon standing over a few days.

m/z 416 (M+H)+ [ES+]

¹H NMR (CDCl₃) σ 2.2 (m, 6H [CH₂—CH₂—COO-tbu]₃) 1.6 (m, 6H [CH₂—CH₂—COO-tbu]₃) 1.45 (s, 27H [CH₂—CH₂—COO-tbu]₃)

IR (KBr) 3376s (NH₂) 2978s (CH₂), 1730s (C=O) cm⁻¹

4-Acetylamino-4-(2-tert-butoxycarbonyl-ethyl)-heptanedioic acid di-tert-butyl ester (63)

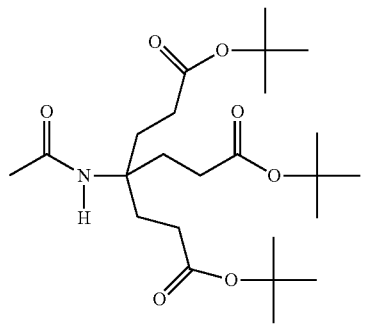 [SMILES: CC(=O)NC(CCC(=O)OC(C)(C)C)(CCC(=O)OC(C)(C)C)CCC(=O)OC(C)(C)C]

To 5 ml CH₂Cl₂ was added 1 g of triester 62 (2.4 mmol, 1 equiv) and 0.3 g triethylamine (2.9 mmol, 1.2 equiv.) The solution was cooled to 0° C. with an ice bath and 0.23 g acetyl chloride (2.9 mmol, 1.2 equiv) was added dropwise. The solution was stirred for a further 4 hours and allowed to warm slowly to room temperature. The solution was poured into a separating funnel and washed with 2×15 ml HCl (5% aqueous) and 1×15 ml concentrated NaCl. The solution was dried over Na₂SO₄ and the solvent was removed in vacuo. The residue was dissolved in minimal EtOAc and loaded onto a silica column, where it was purified by column chromatography with EtOAc and hexane (1:1) to give 0.79 g of a white solid in 72% yield.

m/z 458 (M+H)$^+$ 475 (M+NH$_4$)$^+$ [ES$^+$]

$^1$H NMR (DMSO-d$_6$) σ 7.2 (s, 1H [CONH]) 2.0 (m, 6H [CH$_2$—CH$_2$—COO-tbu]$_3$) 1.8 (s, 3H [CH$_3$—CO]) 1.7 (m, 6H [CH$_2$—CH$_2$—COO-tbu]$_3$) 1.35 (s, 27H [CH$_2$—CH$_2$—COO-tbu]$_3$)

4-Acetylamino-4-(2-carboxy-ethyl)-heptanedioic acid (64)

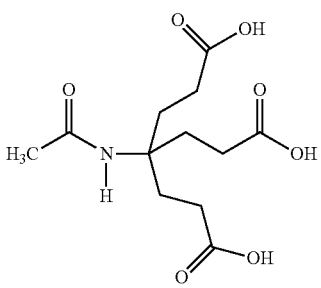 [SMILES: CC(=O)NC(CCC(=O)O)(CCC(=O)O)CCC(=O)O]

1.5 g of triester 63 (3.28 mmol) was added to 20 ml formic acid (96%) and stirred for 4 hours. After this time the formic acid was removed by azeotropic distillation with 5×20 ml portions of toluene. The crude residue was recrystallised from EtOH and petroleum spirit to give 0.9 g of off white crystals in 93% yield.

m/z 290 (M+H)$^+$ [ES$^+$]

$^1$H NMR (DMSO-d$_6$) σ 12 (s, 3H [CH$_2$—COOH]) 7.2 (s, 1H [N—H]) 2.1 (m, 6H [CH$_2$—CH$_2$—COOH]$_3$) 1.8 (m, 6H [CH$_2$—CH$_2$—COO-tbu]$_3$) 1.7 (s, 3H [CH$_3$—CO])

4-Acetylamino-4-{2-[(3-benzyloxy-1,6-dimethyl-4-oxo-1,4-dihydro-pyridin-2-ylmethyl)-carbamoyl]-ethyl}-heptanedioic acid bis-[(3-benzyloxy-1,6-dimethyl-4-oxo-1,4-dihydro-pyridin-2-ylmethyl)-amide] (65)

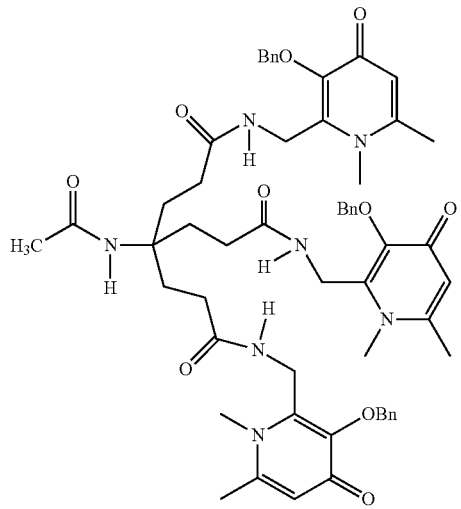 [SMILES: CC(=O)NC(CCC(=O)NCc1c(OCc2ccccc2)c(=O)cc(C)n1C)(CCC(=O)NCc1c(OCc2ccccc2)c(=O)cc(C)n1C)CCC(=O)NCc1c(OCc2ccccc2)c(=O)cc(C)n1C]

To 10 ml anhydrous DMF in a 100 ml round bottomed flask were added 0.4 g 64 (1.38 mmol, 1 equiv) 1.29 g 60 (4.98 mmol, 3.6 equiv) 0.67 g HOBt (4.98 mmol, 3.6 equiv) and 1.03 g DCCI (4.98 mmol, 3.6 equiv.) The mixture was stirred for 48 hours at room temperature under an atmosphere of N$_2$. The solution was filtered to remove the precipitated DCU. DMF was removed in vacuo. The residue was dissolved in methanol and purified by column chromatography (silica gel) with a mobile phase of 4:1 CHCl$_3$/CH$_3$OH. The fractions were combined, dried (Na$_2$SO$_4$) and the solvent was removed in vacuo to give 0.7 g of a white solid in 50% yield.

m/z 1010 (M+H)$^+$ 1032 (M+Na)$^+$ [ES$^+$]

$^1$H NMR (DMSO-d$_6$) σ 8 (t, 3H [CONH]) 7.3 (m, 15H [CH$_2$-Bnz]) 7.15 (s, 1H [CONH]) 6.2 (s, 3H [5-H pyridinone]) 5.05 (s, 6H [CH$_2$-Bnz]) 4.3 (d, 6H [CONH—CH$_2$-pyridinone]) 3.35 (s, 9H [6-CH$_3$ pyridinone]) 2.2 (s, 9H [N—CH$_3$ pyridinone]) 2.0 (m, 6H [CH$_2$—CH$_2$—CONH-pyridinone]) 1.75 (m, 6H [CH$_2$—CH$_2$—CONH-pyridinone]) 1.7 (s, 3H [CH$_3$—CONH-tripod])

4-Acetylamino-4-{2-[(3-hydroxy-1,6-dimethyl-4-oxo-1,4-dihydro-pyridin-2-ylmethyl)-carbamoyl]-ethyl}-heptanedioic acid bis-[(3-hydroxy-1,6-dimethyl-4-oxo-1,4-dihydro-pyridin-2-ylmethyl)-amide] tris hydrochloride salt (52) (CP256)

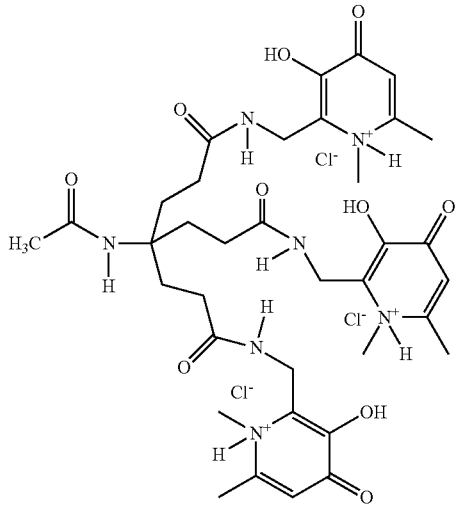 [SMILES: CC(=O)NC(CCC(=O)NCC1=C(O)C(=O)C=C(C)[NH+]1C)(CCC(=O)NCC1=C(O)C(=O)C=C(C)[NH+]1C)CCC(=O)NCC1=C(O)C(=O)C=C(C)[NH+]1C ; [Cl-] ; [Cl-] ; [Cl-]]

0.64 g of 65 (0.63 mmol, 1 equiv) was dissolved in 40 ml CH$_3$OH in a thick walled hydrogenation flask. 2.3 ml of HCl (1.25 M in CH$_3$OH) was added to the solution. 0.2 g of Pd/C catalyst was added and the solution was hydrogenated for 18 hours (room temperature, 40 psi.) The flask was removed with care and the solution filtered to remove Pd/C. The solvent was removed in vacuo. The residue was redissolved in minimal methanol. The product (52) was precipitated with diethylether. Once the precipitate had settled, the supernatant was removed and the precipitate was washed with cold diethyl ether. This process was repeated 3 times and solvent removed in vacuo to give 0.4 g of the tris hydrochloride salt of 52 as a white solid in 74% yield.

m/z 740.4 (M+H)$^+$ 370.7 (M+2H)$^{2+}$ $^1$H NMR (DMSO-d$_6$) σ8.8 (t, 3H [CONH]) 7.25 (s, 1H [CONH]) 7.1 (s, 3H [5-H pyridinone]) 4.5 (d, 6H [CONH—CH$_2$-pyridinone]) 3.8 (s, 9H [6-CH$_3$ pyridinone]) 2.55 (s, 9H [N—CH$_3$ pyridinone]) 2.1 (m, 6H [CH$_2$—CH$_2$—CONH-pyridinone]) 1.8 (m, 6H [CH$_2$—CH$_2$—CONH-pyridinone]) 1.7 (s, 3H [CH$_3$—CONH-tripod])

Example 2

Characterisation of Gallium and Iron Complexes of CP256 and Ga-67 Labelling Procedure Formation of the Ga-CP256 and Fe-CP256 complexes is evident from the mass spectral data shown in Table 1 and Table 2. The protonated form of each complex was detected and the isotopic distribution from the mass spectrum matches the calculated values recorded in table 1. The Ga-CP256 complex has two molecular species for $(M+H)^+$, at m/z 806 and m/z 808, due to gallium having two stable isotopes with atomic masses of 69 and 71. No evidence of Ga-CP256 complexes with Ga:ligand ratios other than 1:1 was found.

The mass spectral data for Fe-CP256 complex match the predicted isotopic distributions.

| Molecular formulae and monoisotopic masses | | |
|---|---|---|
| CP256: | $C_{36}H_{49}N_7O_{10}$ | (M = 739.3541) |
| Ga-CP256: | $C_{36}H_{46}N_7O_{10}Ga$ | (M = 805.2562) |
| Fe-CP256: | $C_{36}H_{46}N_7O_{10}[^{56}Fe]$ | (M = 792.2656) |

TABLE 1

Summary of LC-MS results

| Sample | LC retention time (mins) | Species | m/z (calculated) | m/z (found) |
|---|---|---|---|---|
| CP256 | 5.1 | $(M + H)^+$ | 740.3614 | 740.3631 |
| | | $(M + 2H)^{2+}$ | 370.6843 | 370.6865 |
| Ga-CP256 | 5.3 | $(M + H)^+$ | 806.2635 | 806.2636 |
| | | $(M + Na)^+$ | 828.2454 | 828.2448 |
| | | $(M + 2H)^{2+}$ | 403.6354 | 403.6367 |
| | | $(M + H + Na)^{2+}$ | 414.6263 | 414.6266 |
| | | $(M + 2Na)^{2+}$ | 425.6173 | 425.6180 |
| Fe-CP256 | 5.4 | $(M + H)^+$ | 793.2728 | 793.2733 |
| | | $(M + Na)^+$ | 815.2548 | 815.2545 |
| | | $(M + 2H)^{2+}$ | 397.1401 | 397.1401 |
| | | $(M + H + Na)^{2+}$ | 408.1310 | 408.1316 |
| | | $(M + 2Na)^{2+}$ | 419.1220 | 419.1230 |

Radiolabelling CP256 with Ga-67 gave a product whose HPLC showed a single radioactive peak with an elution time identical with that of the "cold" Ga-CP256 complex.

TABLE 2

Calculated and experimental isotopic distributions of Ga-CP256 and Fe-CP256 and the CP256 ligand.

| m/z: Calculated/(found) | % Relative abundance: Calculated/(found) |
|---|---|
| Isotopic distribution for $(C_{36}H_{46}N_7O_{10}Ga + H)^+$ | |
| 806.2635/(806.2635) | 100.00/(100.00) |
| 807.2635/(807.2655) | 42.59/(41.73) |
| 808.2635/(808.2634) | 77.28/(76.99) |
| 809.2635/(809.2653) | 30.34/(29.20) |
| 810.2635/(810.2670) | 7.56/(7.36) |
| Isotopic distribution for $(C_{36}H_{46}N_7O_{10}Fe + H)^+$ | |
| 791.2775/(791.2779) | 6.33/(5.47) |
| 792.2775/(792.2768) | 2.69/(2.92) |
| 793.2775/(793.2741) | 100.00/(100.00) |
| 794.2775/(794.2765) | 44.72/(42.20) |
| 795.2775/(795.2782) | 12.14/(10.88) |
| Isotopic distribution for $(C_{36}H_{49}N_7O_{10} + 2H)^{2+}$ | |
| 370.6843/(370.6858) | 100.00/(100.00) |
| 371.1843/(371.1869) | 42.64/(51.38) |
| 371.6843/(371.6887) | 10.93/(14.26) |

Experimental Details
Preparation of Complexes
Ga-CP256

1 mg CP256 was dissolved in 1 ml methanol to give a ligand concentration of 1.18 mM (based on tris HCl adduct of CP256 with RMM of 848). This solution was added to 0.3 mg anhydrous $Ga(NO_3)_3$ (RMM 255) to give a 1:1 metal to ligand stoichiometry at a concentration of 1.18 mM.

Fe-CP256

The $Fe^{3+}$ complex was produced in an analogous procedure to the $Ga^{3+}$ complex, but with $Fe(NO_3)_3.9H_2O$ (RMM=386) as the metal source.

Sample Analysis

Samples were analysed by LC-MS. The HPLC system was an Agilent 1200 system with degasser, quaternary pump, UV-visible variable wavelength detector, and an autosampler. The mass spectrometer was an Agilent 6520 Accurate-Mass Q-TOF LC/MS. Samples were acquired using Agilent Masshunter workstation acquisition software and data were analysed using Agilent Masshunter Qualitative analysis software. The HPLC column used was an Agilent Zorbax SB C18 cartridge column (2.1 mm×30 mm, 3.5 µm.) The eluent flow rate was 0.5 ml/min and the mobile phase was a gradient using mass spectrometry grade reagents: $A=H_2O+0.1\%$ formic acid (Fluka, 34673) and B=methanol+0.1% formic acid (Fluka, 34671). The gradient is given in Table 3. Spectra were acquired using electrospray ionisation in positive mode using reference mass correction with hexakis(1H,1H,3H-tetrafluoropropoxy)phosphazine ($C_{18}H_{18}N_3O_6P_3F_{24}$, m/z=922.0098 $[M+H]^+$). Isotopic distributions were calculated using Molecular Weight Calculator version 6.46.

TABLE 3

Gradient for LC-MS analysis of CP256 and the $Fe^{3+}$ and $Ga^{3+}$ complexes.

| Time (min) | A (%) | B (%) |
|---|---|---|
| 0 | 95 | 5 |
| 1 | 95 | 5 |
| 10 | 5 | 95 |
| 20 | 5 | 95 |
| 23 | 95 | 5 |
| 30 | 95 | 5 |

HPLC of Radiolabelled Samples
HPLC Analysis

HPLC analyses were carried out with FC3600 detector and γ detector probe connected in series. The HPLC system, was an Agilent 1200 series with quadruple pump, degasser, UV detector and manual syringe injector. The HPLC column used for all analyses was an Agilent Eclipse XDB-C18 (5 µm, 4.6 mm×150 mm) with a guard column. The analytical software used for radio-TLC and radio-HPLC was Laura (Lablogic). All general reagents and consumables were purchased from Sigma-Aldrich or from Fisher Scientific. $^{67}$Ga-Citrate solution for injection was obtained from Mallinkrodt Medical, 74 MBq/ml (at ref. date; contains 6.5 mM sodium citrate, 135 mM NaCl, 0.9% Benzyl alcohol).

Radiolabelling Procedure for HPLC Analysis

A 1 mg/ml stock solution of CP256 was prepared in PBS buffer in a 1 ml plastic microcentrifuge tube. Radiolabelling solutions were prepared by adding a 10 µl aliquot of the stock solution to 90 µl of labelling buffer in a plastic microcentrifuge tube to give a total ligand concentration of 0.1 mg/ml in 100 µl. This solution was radiolabelled by adding 10 µl $^{67}$Ga-citrate. Radiolabelling conditions are shown in table 4.

TABLE 4

Radiolabelling conditions for CP256 with $^{67}$Ga

| LIGAND | LABELLING BUFFER | LABELLING TEMPERATURE | LABELLING TIME | LIGAND CONC. (M) | MEASURED pH |
|---|---|---|---|---|---|
| CP256 | PBS | 25° C. | 1 min | $1.18 \times 10^{-4}$ | 6.6 |

HPLC Mobile Phase

Linear gradient of 10% B at 0 minutes to 90% B at 15 minutes. (A=0.1% TFA in H$_2$O, B=0.1% TFA in Methanol.) The flow-rate was 1 ml/min.

HPLC Sample Injection

20 µl of the sample was injected manually into the HPLC using a 25 µl HPLC syringe.

Example 3

CP256 Labelling Efficiency with Ga-67 Data

The radiolabelling results in table 5, measured by Thin Layer Chromatography (TLC) show that CP256 radiolabels with $^{67}$Ga at room temperature at lower concentrations than DOTA does at elevated temperature, with 100% radiolabelling at a concentration as low as 10 µM whereas the radiolabelling yield for DOTA at 10 µM is only 35%. These results are shown graphically in FIG. 1.

TABLE 5

Radiolabelling yields of $^{67}$Ga-CP256 and $^{67}$Ga-DOTA. Calculated from TLC analysis.

| LIGAND CONCENTRATION | RADIOTRACER LABELLING YIELD | |
|---|---|---|
| | CP256 | DOTA |
| 1 mM | 100 | 100 |
| 100 µM | 100 | 100 |
| 10 µM | 100 | 35 |
| 1 µM | 84 | 0 |
| 100 nM | 0 | 0 |
| 10 nM | 0 | 0 |

Experimental Details

All general reagents and consumables were purchased from Sigma-Aldrich or from Fisher Scientific. Specialist chemicals and consumables were purchased as follows: Acetate buffer solution pH 4.6 (Sigma Aldrich 31048-1L); $^{67}$Ga-Citrate solution for injection (Mallinkrodt Medical) 74 MBq/ml (at ref. date; contains 6.5 mM sodium citrate, 135 mM NaCl, 0.9% Benzyl alcohol); glass TLC plates (silica gel 60, F$_{254}$, 250 mm×750 mm) (Merck); ITLC-SG strips (Pall Sciences).

Procedure for Spotting and Running TLC Plates

Silica TLC plates and ITLC-SG strips were spotted with 1 µl of radiolabelled complex at the origin, which was marked at 5 mm in pencil. Spots were allowed to dry on silica gel TLC plates but not for ITLC-SG strips. The plates were placed in a developing chamber (100 ml wide necked sample bottle) filled with a 3 mm depth of the mobile phase. Stationary phases and mobile phases are listed in table 8. The TLC plate was developed until the solvent front had reached a distance of up to 65 mm. The plates were removed from the developing chamber and dried in an oven set at 80° C. Radiochemical yields were determined using either Laura software or the instant imager software.

TLC and ITLC analyses were carried out on a Mini-Scan TLC scanner with FC3600 detector and γ detector probe. The analytical software used was Laura (Lablogic). Radioactive samples were counted for 10 seconds (window 101-110) on a 1282 Compugamma Gamma Counter (LKB Wallac) using Ultroterm software. The dose calibrator used for measuring radioactivity in samples was a CRC-25R (Capintec.) Electronic autoradiography was performed on a Packard Instant Imager with Imager version 2.05 software. The gas mixture was 1% isobutane, 2.5% carbon dioxide and 96.5% argon (Air products.)

Radiolabelling Procedure for Radiochemical Yield Determination by TLC Analysis 1.25 mM stock solutions of each ligand were prepared in the appropriate labelling buffer, as listed in table 6. The stock solution was diluted 10 fold by successive addition of the radiolabelling buffer to create extra solutions with ligand concentrations of 125 µM, 12.5 µM, 1.25 µM, 125 nM and 12.5 nM. Eighty microliters of each solution was added to a plastic microcentrifuge tube and radiolabelled with 20 µl of $^{67}$Ga-Citrate (1.5 MBq) to produce radiolabelled solutions with final ligand concentrations of 1 mM, 100 µM, 10 µM, 1 µM and 100 nM. A metal heater block (containing oil in the wells) was used to heat the $^{67}$Ga-DOTA solution. Radiolabelling conditions are shown in table 6.

TABLE 6

Radiolabelling conditions for each ligand. Final concentrations of each ligand in the labelling mixture were 1 mM, 100 µM, 10 µM, 1 µM, 100 nM and 10 nM.

| LIGAND | LABELLING BUFFER | LABELLING TEMPERATURE | LABELLING TIME | MEASURED pH |
|---|---|---|---|---|
| DOTA | Acetate | 80° C. | 45 min | 4.6 |
| CP256 | PBS | 25° C. | 1 min | 6.6 |

Example 4

CP256 Labelled with Ga-67—Kinetic Stability

Stability of $^{67}$Ga-CP256 in Apo-Transferrin by PD10 Size Exclusion

Figure 2:
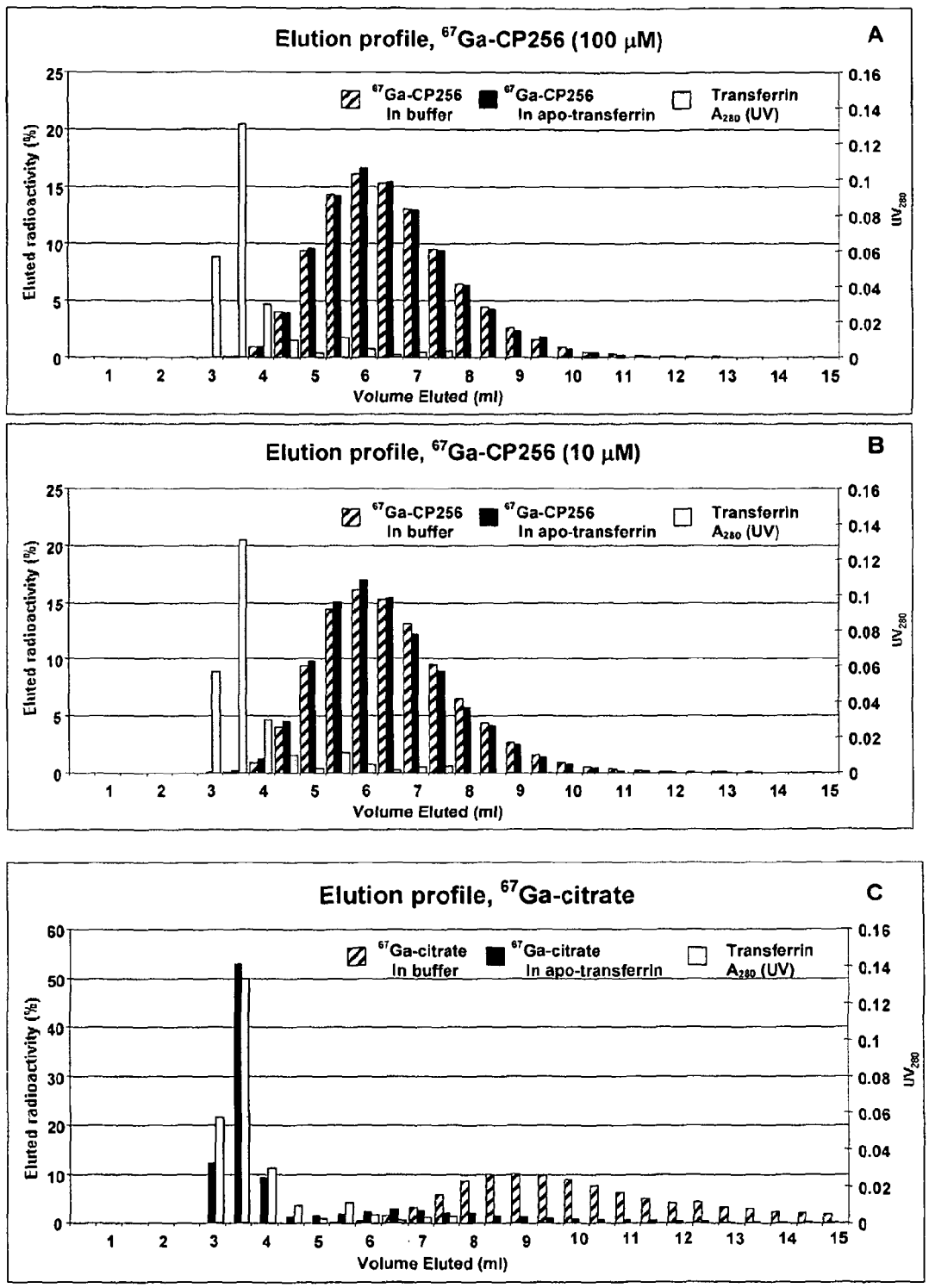
FIG. 2. shows the elution profiles of $^{67}$Ga-CP256 from a PD10 column for radiolabelled solutions at 2.27 μM (A) and 0.227 μM (B) of CP256 after incubation with apotransferrin, compared to $^{67}$Ga-citrate (C).

FIG. 2 shows the elution profiles of $^{67}$Ga-CP256 from a PD10 column for radiolabelled solutions at 100 µM (A) and 10 µM (B) of CP256. After dilution and incubation in apo-transferrin, the concentrations of CP256 in these solutions were 227 µM and 2.27 nM respectively. After 4 hours incubation in apo-transferrin, the profile is unchanged from that of the incubation in the reference buffer, indicating no binding of $^{67}$Ga to transferrin or loss of $^{67}$Ga from the ligand, for either of the 2.27 µM or 227 nM solutions.

Radiopharmaceutical Stability Using 30 kDa MWCO Filters

Figure 3:
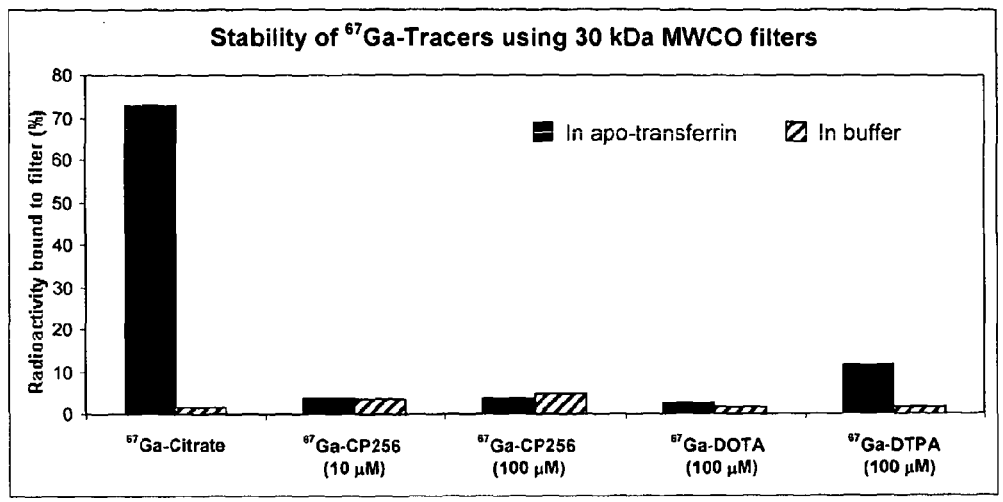
FIG. 3. shows retention of $^{67}$Ga-citrate, $^{67}$Ga-CP256, $^{67}$Ga-DOTA and $^{67}$Ga-DTPA to 30 kDa MWCO filters, after incubation with apotransferrin.

As shown in table 7 and FIG. 3, residual binding of all of the radiolabelled tracers to the filter membrane was low (≤5%.) Seventy three percent of the radioactivity from the $^{67}$Ga-citrate incubation in apo-transferrin was associated with the MWCO filter after 4 hours. The MWCO method also showed negligible transchelation of $^{67}$Ga to apo-transferrin (≤1%) in the $^{67}$Ga-CP256 and $^{67}$Ga-DOTA solutions over the 4 hour incubation period. In the case of the 100 µM CP256 solution (2.27 µM in apo-transferrin) the background binding from the incubation in the reference buffer was higher by 1%. $^{67}$Ga-DTPA showed some dissociation over the 4 hour incubation period, with 10% extra binding of the radioactivity in this solution to the filter when compared with the solution in the reference buffer.

TABLE 7

Binding of $^{67}$Ga-citrate, $^{67}$Ga-CP256, $^{67}$Ga-DOTA and $^{67}$Ga-DTPA to 30 kDa MWCO filters.

| | % RADIOACTIVITY BOUND TO MWCO FILTER | |
| --- | --- | --- |
| TRACER | IN REFERENCE BUFFER | APO-TRANSFERRIN INCUBATION, AFTER 4 HOURS |
| $^{67}$Ga-CITRATE | 1.7 ± 0.5 | 73.0 ± 4.1 |
| $^{67}$Ga-CP256 (10 µM) | 3.5 ± 1.3 | 3.9 ± 0.8 |
| $^{67}$Ga-CP256 (100 µM) | 4.9 ± 0.5 | 3.8 ± 0.5 |
| $^{67}$Ga-DOTA | 1.5 ± 1.7 | 2.6 ± 0.8 |
| $^{67}$Ga-DTPA | 1.5 ± 0.6 | 11.4 ± 1.4 |

Experimental Details

Specialist chemicals and consumables were purchased as follows: human apo-transferrin (Sigma Aldrich T5391-10MG); Sartorius Vivaspin 500 30 kDa MWCO filters (Fisher Scientific FDP-875-025B); PD10 columns (GE Healthcare 17-0851-01); UV spectrophotometry of apo-transferrin was performed on a Cary UV spectrophotometer with Cary WinUV software. The wavelength was set at 280 nm.

TABLE 8

Details of mobile phases and stationary phases used for TLC and ITLC quality control of $^{67}$Ga-CP256, $^{67}$Ga-DOTA and $^{67}$Ga-DTPA.

| RADIO-TRACER | MOBILE PHASE | STATIONARY PHASE |
| --- | --- | --- |
| $^{67}$Ga-CP256 | Methanol/citric acid (0.5M)/ammonium formate (10% w, v) [40/20/40] | Silica gel |
| $^{67}$Ga-DOTA | Sodium citrate (aq) [0.3M] | Silica gel |
| $^{67}$Ga-DTPA | Methanol/citric acid (0.5M) ammonium formate (10% w, v) [40/20/40] | Silica gel |
| | Methanol/acetic acid (0.5M) ammonium formate (10% w, v) [40/20/40] | Silica gel |
| | Acetic acid [0.5M] | Silica gel |
| | 9/1/0.1 methanol/glacial acetic acid/sodium citrate [0.3M] | ITLC-SG |
| | Sodium citrate [0.1M] | ITLC-SG |

Preparation of $^{67}$Ga-Citrate Reference Solution

A reference solution of $^{67}$Ga-citrate was produced by incubating 20 µl $^{67}$Ga-citrate in 200 µl PBS. This solution was incubated at 37° C. in a metal heating block and samples were removed for analysis in the same manner as for the serum incubation.

Preparation of Apo-Transferrin Solution 50 mM TRIS-HCl buffer (pH 7.5) was prepared by dilution of a 1 M stock solution. Sodium bicarbonate was added to a concentration of 25 mM. A 2.5 mg/ml (32 µM) solution of apo-transferrin was prepared in this buffer.

Preparation of $^{67}$Ga-Tracers

Solutions of all tracers were radiolabelled at a concentration of 100 µM. A 10 µM CP256 solution was also prepared. See table 9 for radiolabelling conditions.

A 10 µl aliquot of each radiolabelled tracer was added to 30 µl of an appropriate buffer to neutralise the pH to between 7 and 7.5. This buffer was 2 M TRIS-HCl (pH 7.5) in the case of those tracers labelled in the acetate buffer. For preparations of $^{67}$Ga-CP256 and $^{67}$Ga-Citrate the buffer was PBS. Details can be seen in Table 9.

TABLE 9

Tracer radiolabelling conditions.

| LIGAND | LIGAND CONC. AFTER RADIO-LBELLING | RADIO-LABELLING BUFFER | DILUTION BUFFER | FINAL LIGAND CONC. |
| --- | --- | --- | --- | --- |
| DOTA | 100 µM | Acetate | TRIS | 25 µM |
| DTPA | 100 µM | Acetate | TRIS | 25 µM |
| CP256 | 100 µM | PBS | PBS | 25 µM |
| | 10 µM | PBS | PBS | 2.5 µM |

Tracer Incubation in Apo-Transferrin

Apo-transferrin solution (200 µl) in a plastic microcentrifuge tube was incubated at 37° C. in a metal heating block. To this was added 20 µl of each pH-neutralised tracer. 20 µl of each tracer was also incubated in a reference buffer (containing no apo-transferrin) of 50 mM TRIS-HCl containing 25 mM sodium bicarbonate.

Tracer Incubation in Reference Buffer

The 50 mM TRIS-HCl solution (200 µl, not containing apo-transferrin) was incubated in a heating block at 37° C. The appropriate pH adjusted tracer (20 µl) was added to the incubation. Aliquots were taken at appropriate intervals for analysis.

Gel Filtration Using a PD10 Column.

Apo-Transferrin Incubations

Equilibration and elution of PD10 columns was with 25 mM sodium bicarbonate added to PBS elution buffer. The standard elution profiles of $^{67}$Ga-citrate, $^{67}$Ga-CP256, $^{67}$Ga-DOTA and $^{67}$Ga-DTPA were determined by adding 20 µl of each tracer that had been incubated in the reference buffer (50 mM TRIS-HCl containing 25 mM sodium bicarbonate) and eluting the columns as described above.

To Calculate the Percentage of Total Eluted Activity for Each 0.5 ml Fraction

Total eluted radioactivity for each column was calculated by adding together the counts for each of the 30 fractions. Eluted activity for each fraction was then calculated by the following equation:

$$\text{Counts per fraction}/\text{Total counts(for all 30 fractions)} \times 100$$

UV Elution Profile of Apo-Transferrin from a PD10 Gel Filtration Column

The elution profile of Transferrin from a PD10 column was determined by UV spectrophometry. Apo-transferrin (non radioactive, 500 µl of the 2.5 mg/ml solution) was loaded onto a PD10 column, eluted with PBS buffer and 0.5 ml fractions were collected. The samples were loaded into a 1 ml quartz cuvette and diluted to 0.9 ml with an extra 0.4 ml of PBS. Absorbance was determined at 280 nm with PBS as a reference standard.

Determination of Tracer Stability Using 30 kDa MWCO Microcentrifuge Filters

PBS (100 µl, containing 25 mM bicarbonate) was applied to the top section (filter section) of the tube. The incubation solution (5 µl) for each tracer (after 4 hours) was added and the tube was spun in a microcentrifuge at 10,000 g for 8 minutes. Another 100 µl PBS was applied to wash and the tube was spun again at 10,000 g for a further 8 minutes. The filter section of the tube was removed and counted separately from the tube in a gamma counter. Percentage binding of the radioactivity to the MWCO filter was calculated using the following equation:

Counts from filter section/Counts from filter section+ counts from tube section×100

The analysis was done in triplicate after 4 hours for the apo-transferrin incubations. The analysis was done 6 times (6 tubes) for the incubations in the 50 mM TRIS-HCl reference buffer. Average values were taken as described above.

Example 5

Synthesis of CP256-maleimide Conjugates

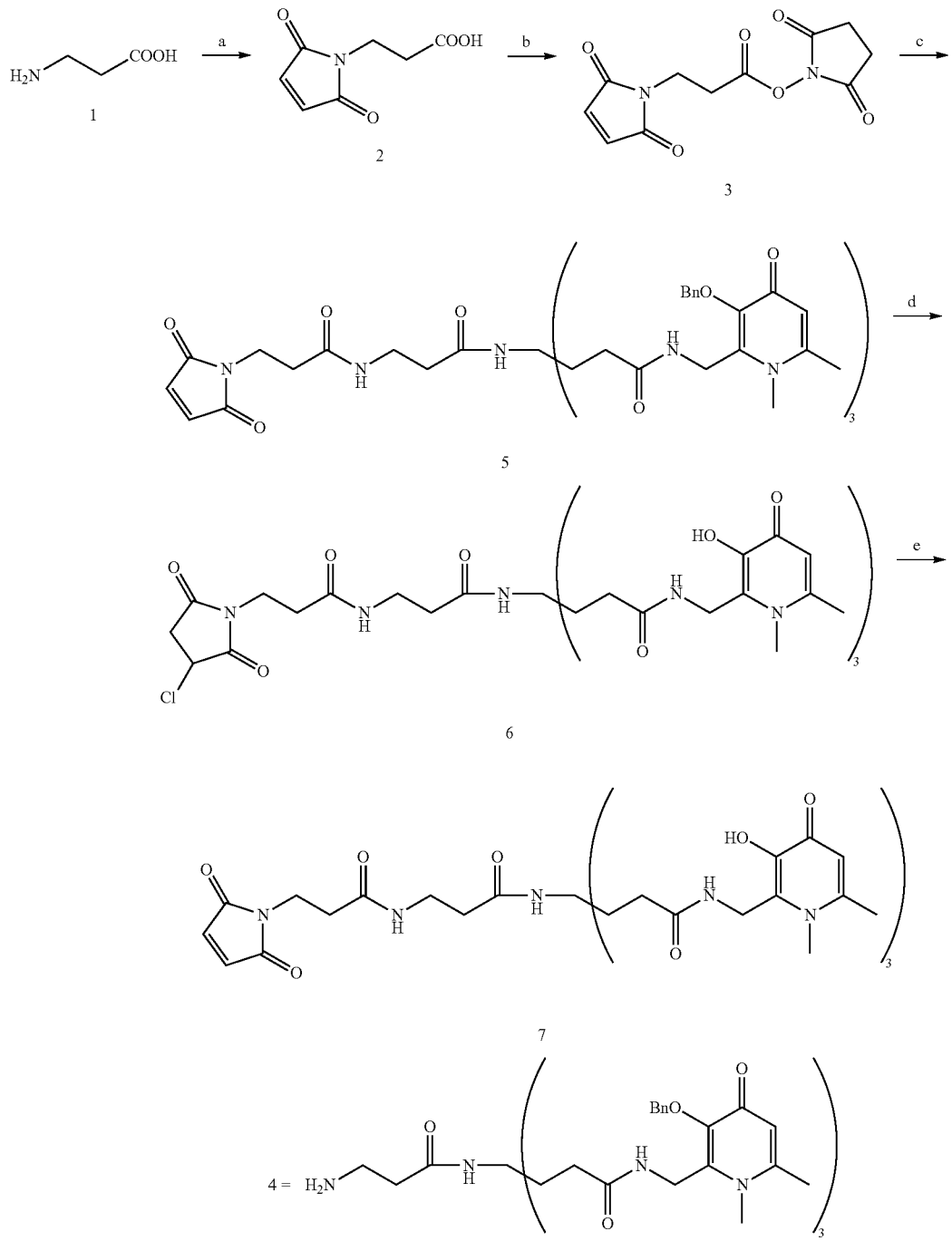

a) maleic anhydride/DMF; b) DCC/NHS/DMF; c) 4/DMF; d) BCl₃/DCM; e) Et₃N/DCM.

Experimental Details

The synthesis of compound 4 has been reported previously (Zhou T. et al., J Med. Chem. 2006, 49, 4171-4182).

Synthesis of succinimido 3-maleimidopropanoate 3

A solution of β-alanine (1.8 g, 20 mmol) and maleic anhydride (2 g, 20 mmol) in DMF (30 mL) was stirred at room temperature for 3 h. After the solid was completely dissolved, N-hydroxysuccinimide (NHS; 2.3 g, 20 mmol) and dicyclohexylcarbodiimide (DCC; 4.6 g, 24 mmol) was added into the solution and the mixture was stirred at room temperature overnight. The solution was filtered and the precipitate was washed with water (100 ml) and dichloromethane (100 ml). The filtrate was collected and the organic layer was washed with 3×50 ml 5% NaHCO$_3$ and one time with brine. The organic layer was dried with Na$_2$SO$_4$ and dichloromethane removed under reduced pressure to obtain a white solid (55%). This solid does not need further purification and can be directly used for next coupling step. $^1$H NMR (CDCl$_3$, 400 MHz): δ 2.82 (s, 4H, two succinimido-CH$_2$), 3.02 (t, J=7.0 Hz, 2H, COCH$_2$), 3.94 (t, J=7.0 Hz, 2H, NCH$_2$), 6.74 (s, 2H, two CH).

Synthesis of Compound 5

The activated acid 3 (6 mmol) and amine 4 (5 mmol) in anhydrous DMF (50 ml) was stirred at room temperature for one day. The solvent was removed under reduced pressure and the residue was purified on a silica gel column using chloroform:methanol (8:2) as an eluent to afford a white foam (81%). $^1$H NMR (CDCl$_3$, 400 MHz): δ 2.05 (brs, 6H, CH$_2$), 2.15 (s, 9H, CH$_3$), 2.23 (brs, 2H, CH$_2$), 2.29 (brs, 6H, CH$_2$), 2.41 (t, J=6.6 Hz, 2H, CH$_2$), 3.32 (brs, 2H, CH$_2$), 3.36 (s, 9H, CH$_3$), 3.73 (t, J=6.6 Hz, 2H, CH$_2$), 4.35 (s, 6H, CH$_2$), 4.87 (s, 6H, CH$_2$), 6.10 (s, 3H, CH), 6.65 (s, 2H, CH), 6.76 (brs, 1H, NH), 7.23-7.30 (m, 15H, ArH), 7.72 (brs, 3H, NH). $^{13}$C NMR (CDCl$_3$, 100 MHz): 20.81 (CH$_3$), 30.70 (CH$_2$), 31.71 (CH$_2$), 34.43 (CH$_2$), 34.62 (CH$_2$), 34.82 (CH$_2$), 36.31 (CH$_3$), 36.68 (CH$_2$), 57.99, 73.42 (CH$_2$), 118.25 (CH), 128.30 (CH), 128.52 (CH), 128.58 (CH), 134.23 (CH), 136.97, 141.05, 146.35, 148.04, 170.43, 170.66, 171.70, 173.10, 173.23. ESI-MS: 1190.40 (M+1)$^+$ Synthesis of Compound 6

To the benzyl protecting compound 5 in anhydrous DCM under N$_2$ was added boron trichloride (12 equiv) in ice-bath and the mixture was stirred at room temperature for 2 days. The excess BCl$_3$ was quenched by adding MeOH followed by 1 mL concentrated hydrochloric acid. The mixture was evaporated to obtain brown solid, which dissolved in methanol and precipitated with the addition of acetone. This procedure was repeated three times to afford white solid (72%). $^1$H NMR (DMSO-d$_6$, 400 MHz): δ 1.75-1.84 (m, 6H, CH$_2$), 2.08-2.13 (m, 6H, CH$_2$), 2.21 (t, J=7.1 Hz, 2H, CH$_2$), 2.32 (t, J=7.5 Hz, 2H, CH$_2$), 2.57 (s, 9H, CH$_3$), 2.85 (dd, J=4.1, 8.3 Hz, 1H, one H of maleic CH$_2$), 3.16 (q, J=6.5 Hz, 2H, CH$_2$), 3.34 (dd, J=8.5, 18.3 Hz, 1H, one H of maleic CH$_2$), 3.58 (t, J=7.5 Hz, 2H, CH$_2$), 3.89 (s, 9H, CH$_3$), 4.57 (d, J=5.0 Hz, 6H, CH$_2$), 4.99 (dd, J=4.1, 8.5 Hz, 1H maleic CH), 7.28 (s, 3H, CH), 7.30 (brs, 1H, NH), 8.09 (t, J=5.6 Hz, 1H, NH), 8.92 (t, J=5.1 Hz, 3H, NH). $^{13}$C NMR (DMSO-d$_6$, 100 MHz): δ 20.56 (CH$_3$), 29.26, (CH$_2$), 29.98 (CH$_2$), 32.67 (CH$_2$), 34.71 (CH$_2$), 35.27 (CH$_2$), 35.58 (CH$_2$), 35.83 (CH$_2$), 39.00 (CH$_2$), 39.05 (CH$_3$), 49.82 (CH), 56.79, 112.73 (CH), 139.90, 142.69, 148.55, 159.59, 169.12, 170.08, 173.18, 173.36, 173.44. ESI-MS: 956.27 (M+1)$^+$. HRMS: Calcd for C$_{44}$H$_{59}$ClN$_9$O$_{13}$ (M+1)$^+$, 956.3921. Found, 956.3953.

Synthesis of Compound 7

To compound 6 (20 mg) in DCM (20 mL) was added excess Et$_3$N and the mixture was stirred at room temperature overnight. After evaporation to remove the solvent, the residue was loaded on a solid phase extraction column by dissolving in 1 ml 0.1% formic acid solution. The column was firstly washed with 0.1% formic acid (10 mL) to remove triethylamine hydrochloride salt, followed by elution of methanol (10 mL). The fraction of the methanol solution was concentrated and dried by vacuum oven to yield a white powder (80%). $^1$H NMR (CD$_3$OD, 400 MHz): δ 1.94-2.03 (m, 6H, CH$_2$), 2.20-2.29 (m, 6H, CH$_2$), 2.32 (t, J=6.3 Hz, 2H, CH$_2$), 2.38 (s, 9H, CH$_3$), 2.42 (t, J=7.0 Hz, 2H, CH$_2$), 3.31 (q, J=6.7 Hz, 2H, CH$_2$), 3.66 (s, 9H, CH$_3$), 3.69 (t, J=7.1 Hz, 2H, CH$_2$), 4.58 (s, 6H, CH$_2$), 5.25 (s, 3H, NH), 6.29 (s, 3H, CH), 6.81 (s, 2H, CH). $^{13}$C NMR (CD$_3$OD, 100 MHz): δ 21.03 (CH$_3$), 30.11, (CH$_2$), 31.48 (CH$_2$), 35.43 (CH$_2$), 35.69 (CH$_2$), 36.02 (CH$_2$), 37.21 (CH$_3$), 37.49 (CH$_2$), 59.17, 63.70 (CH$_2$), 114.58 (CH), 129.59, 132.25, 135.57 (CH), 147.38, 148.87, 171.12, 172.26, 172.98, 173.33, 175.89. ESI-MS: 920.33 (M+1)$^+$. HRMS: Calcd for C$_{44}$H$_{58}$N$_9$O$_{13}$ (M+1)$^+$, 920.4154. Found, 920.4146.

Example 6

Conjugation of CP256-chlorosuccinimide (6) or CP256-maleimide (7) with C2Ac Protein C2A is a small protein that recognises phosphatidylserine displayed on cells undergoing apoptotis. It has been engineered with a cysteine residue to facilitate site-specific labelling with thiol-reactive agents (see Tavare R, Torres Martin de Rosales R, Blower P J, Mullen G E D. Efficient site-specific radiolabeling of a modified C2A domain of synaptotagmin I with [$^{99m}$Tc(CO)$_3$]$^+$: a new radiopharmaceutical for imaging cell death. Bioconjugate Chem 2009; 20:2071-2081). The resulting engineered protein (C2Ac) was conjugated with CP256 using either 6 or 7. The same product was obtained for both conjugation reactions.

The average molecular weight of C2Ac is 14997 and so the C2Ac-(7) conjugate was expected to have an average molecular weight of 15918.44. The found average molecular weight was 15970.85, which corresponds to the C2Ac-(7) conjugate with an additional iron atom and without 3 hydrogen atoms.

Experimental Details

C2Ac (2 mg in a solution of 2 mg/mL) was treated with a 3:1 molar excess of chlorosuccinimide-hexadentate chelator (6) or maleimide-hexadentate chelator (7) for 4 hours at room temperature. The mixture was purified using a PD-10 column pre-equilibrated with PBS that had been stored over Chelex and analysed by LC-MS.

Example 7

Figure 4:
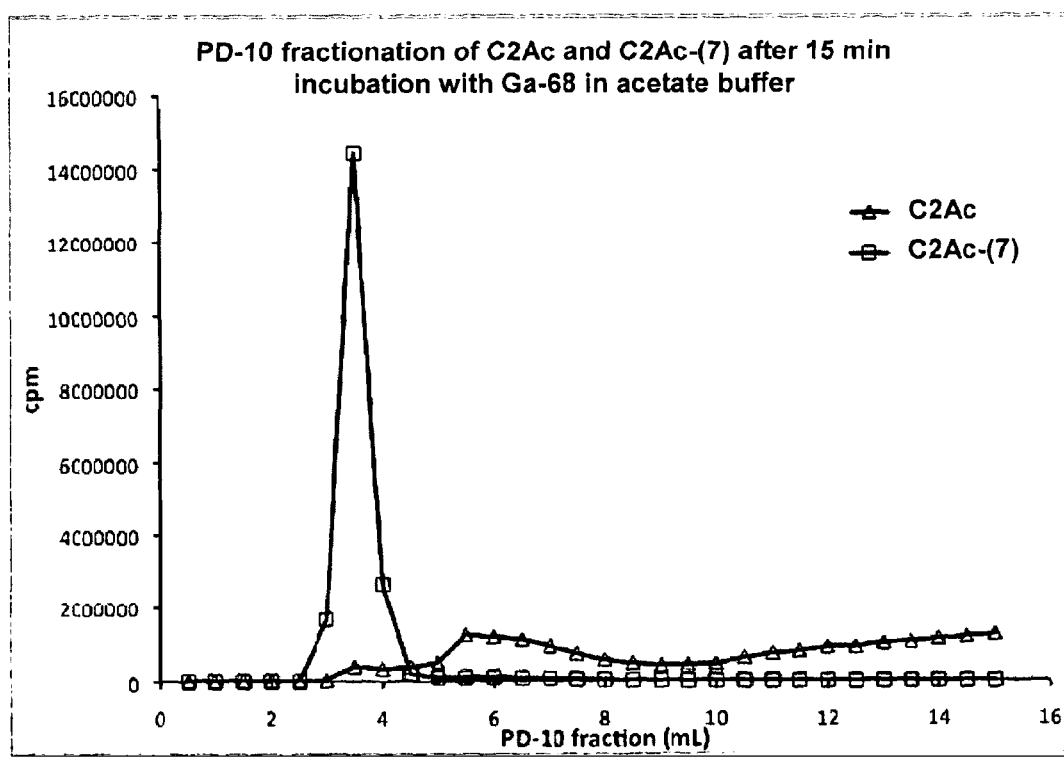
FIG. 4. shows the radioactive elution profile, using a PD10 size exclusion cartridge, of C2Ac and C2Ac-(7) after 15 minutes incubation with Gallium-68 in acetate buffer.
Figure 5:
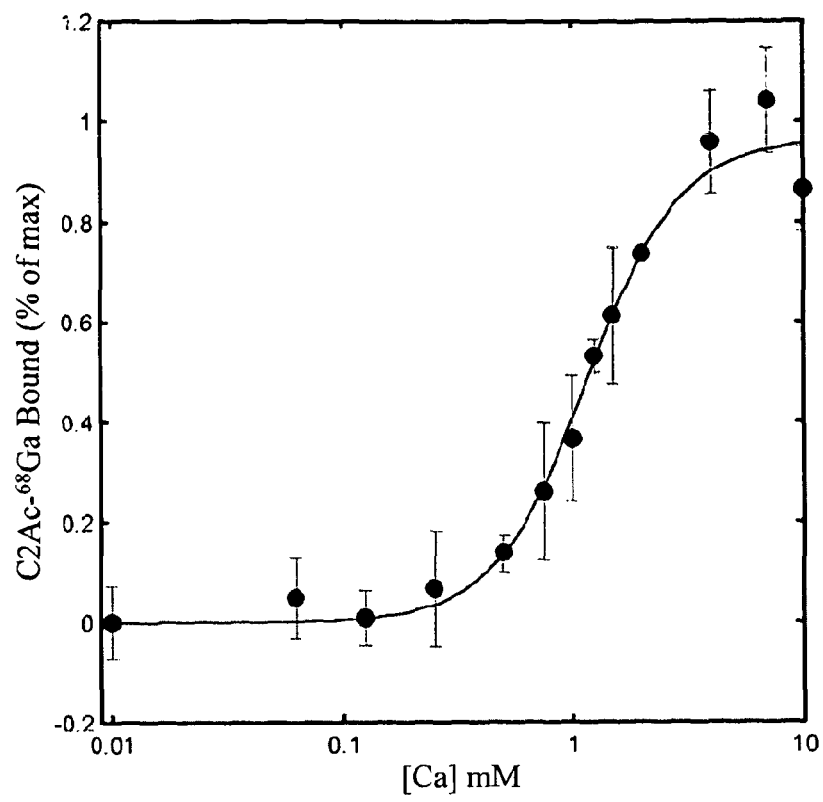
FIG. 5. The $^{68}$Ga-labelled conjugate showed specific calcium dependent binding to phosphatidylserine (PS) in a red blood cell binding assay FIG. 6. shows a PET scan of a mouse 90 minutes after administration of (a) C2Ac-(7)~$^{68}$Ga and (b) unchelated "free" $^{68}$Ga.

Labelling of C2Ac Protein Conjugate with $^{68}$Ga and Functional Data on Labelled Protein The C2Ac-(7) conjugate was radiolabelled with $^{68}$Ga according to the method described herein. FIG. 4 shows a high degree of chelation after only 15 minutes of incubation with $^{68}$Ga in acetate buffer. The $^{68}$Ga-labelled conjugate showed specific calcium dependent binding to phosphatidylserine (PS) in a red blood cell binding assay (see FIG. 5)

Experimental Details

Unchelated $^{68}$Ga in buffer, was prepared as follows. The generator was eluted with in 2 ml 0.1M HCl to give 25 MBq $^{68}$Ga eluate. 1.5 ml of conc. HCl (36%) was added to the elution to give a final concentration of 4M HCl to form gallium tetrachloride anion, and the solution passed through an anion exchange column (SAX SPEC, Chromafix 30-PS-HCO3, 45 mg, Macherey-Nagel, Germany), trapping all activity. The column was then washed with 250 µl 5M NaCl and the activity then eluted with 300 µl distilled water and the eluate (pH<1, ~70 MBq) buffered by adding 5 µl of 1M NaOH and 30 µl of 1M ammonium acetate buffer, pH 6, raising pH to 7. 100 µl of PBS, pH 6 was then added.

200 µL of the preconcentrated and buffered $^{68}$Ga solution was added to 100 µg (in 100 µl) of the C2Ac-(7) chelator conjugate. At 5 minute intervals, 2 µl of the mixture was spotted on ITLC-SG and the chromatogram developed using 0.1 M citrate buffer as the mobile phase.

The binding of radiolabeled C2Ac-(7) to PS on red blood cells (RBC) was performed according to a literature method (see Tait, J. F., Gibson, D. F., and Smith, C. (2004) Measurement of the affinity and cooperativity of annexin V-membrane binding under conditions of low membrane occupancy. Anal. Biochem. 329, 112-119). A commercial preparation of preserved human RBC was obtained from Beckman-Coulter (High Wycombe, UK). Calcium titrations of RBC were performed in a buffer of 50 mM HEPES-sodium, pH 7.4, 100 mM NaCl, 3 mM NaN$_3$ with 1 mg/mL BSA as carrier protein. Reactions were prepared with 1 nM $^{68}$Ga labelled C2AcH and calcium; RBC were then added, and the reaction (1 ml) was incubated for 8 min at RT.

The cells were then centrifuged (3 min at 7500 RCF), the supernatant was removed, and the cells were resuspended in 1 ml assay buffer containing the same concentration of calcium used during the incubation step. The cells were centrifuged again, the supernatant was removed, and the pellet was resuspended in 0.7 ml assay buffer plus 10 mM ethylenediaminetetraacetic acid (EDTA) to release $^{68}$Ga labelled C2Ac-(7) bound in a calcium-dependent manner. After centrifugation to remove the RBC, the released labelled C2Ac-(7) in the supernatant was measured using a gamma counter. The EC50 was calculated as described in the literature using the equation $Y=[Ca]^N/([Ca]^N+EC50^N)$ where Y=B/Bmax, B is the observed amount of radiolabelled protein bound at a given calcium concentration, and Bmax is the concentration of radiolabelled protein bound at saturating calcium concentrations.

Curve fitting was performed using a nonlinear curve fit by a routine based on the Levenberg-Marquardt algorithm using Kaleidagraph (Synergy Software, Reading, US).

Example 8

PET Scanning and Biodistribution in Mice with $^{68}$Ga-C2Ac Conjugate

Figure 6:
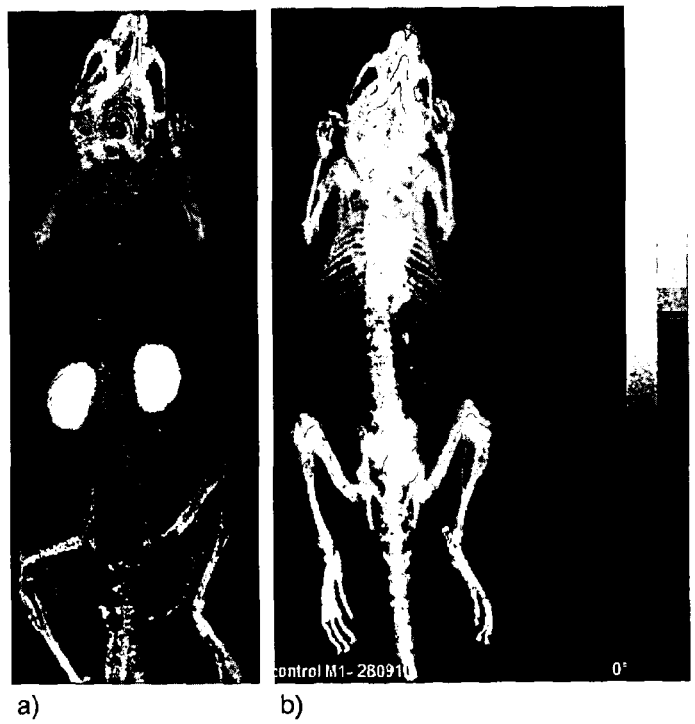

PET images taken at 1.5 h after injection of the $^{68}$Ga-C2Ac-(7) conjugate and unchelated ("free") $^{68}$Ga into mice are shown in FIGS. 6a and 6b respectively. The presence of $^{68}$Ga is shown by bright white areas in the image. Injection of the $^{68}$Ga-C2Ac-(7) conjugate showed rapid clearance of radioactivity from blood and tissues with uptake almost exclusively in kidney with a small amount of activity excreted into the bladder (FIG. 6a). This contrasts with the images obtained with injection of "free" $^{68}$Ga in which activity was seen slowly clearing from blood pool predominantly to remodelling bone (FIG. 6b).

TABLE 10

% of injected radioactivity per gram in mouse tissues 90 min post injection of $^{68}$Ga-C2Ac-(7) conjugate.

|  | Average (n = 4) | Std dev |
|---|---|---|
| Spleen | 0.46 | 0.11 |
| Stomach | 0.77 | 0.31 |
| Intestines | 0.42 | 0.06 |
| Cecum | 0.34 | 0.05 |
| Liver | 0.94 | 0.15 |
| Blood | 0.33 | 0.18 |
| Kidneys | 155.29 | 27.21 |
| Thymus | 0.27 | 0.09 |
| Heart | 0.47 | 0.15 |
| Lungs | 0.63 | 0.15 |
| Muscle | 0.39 | 0.23 |
| Femur (L) | 0.40 | 0.10 |
| Tail | 0.85 | 0.29 |

Experimental Details

The $^{68}$Ga labelled C2Ac-(7) conjugate was synthesised as described above. Unchelated $^{68}$Ga in buffer, was prepared using the pre-concentration (and buffering to pH 7) method described in example 7. TLC analysis was performed. No gallium hydroxide precipitate was detected by the time of injection. The solutions for injection were filtered through a 0.22 µm filter and injected into the tail veins of female C57B/6 mice (n=4, 10 MBq in 100 µl for each animal). PET/CT scans were acquired 90 min post injection using a NanoPET/CT scanner (Bioscan, Paris, France) with PET acquisition time 1800 s, coincidence relation: 1-3. Image reconstruction: OSEM with SSRB 2D LOR, energy window: 400-600 keV, filter: Ramlak cutoff 1, number of iterations/subsets: 8/6. Animals were killed at 90 min and explanted organs counted in a gamma counter to determine biodistribution.

Example 9

Labelling of CP256 with $^{68}$Ga in Serum

Figure 7:
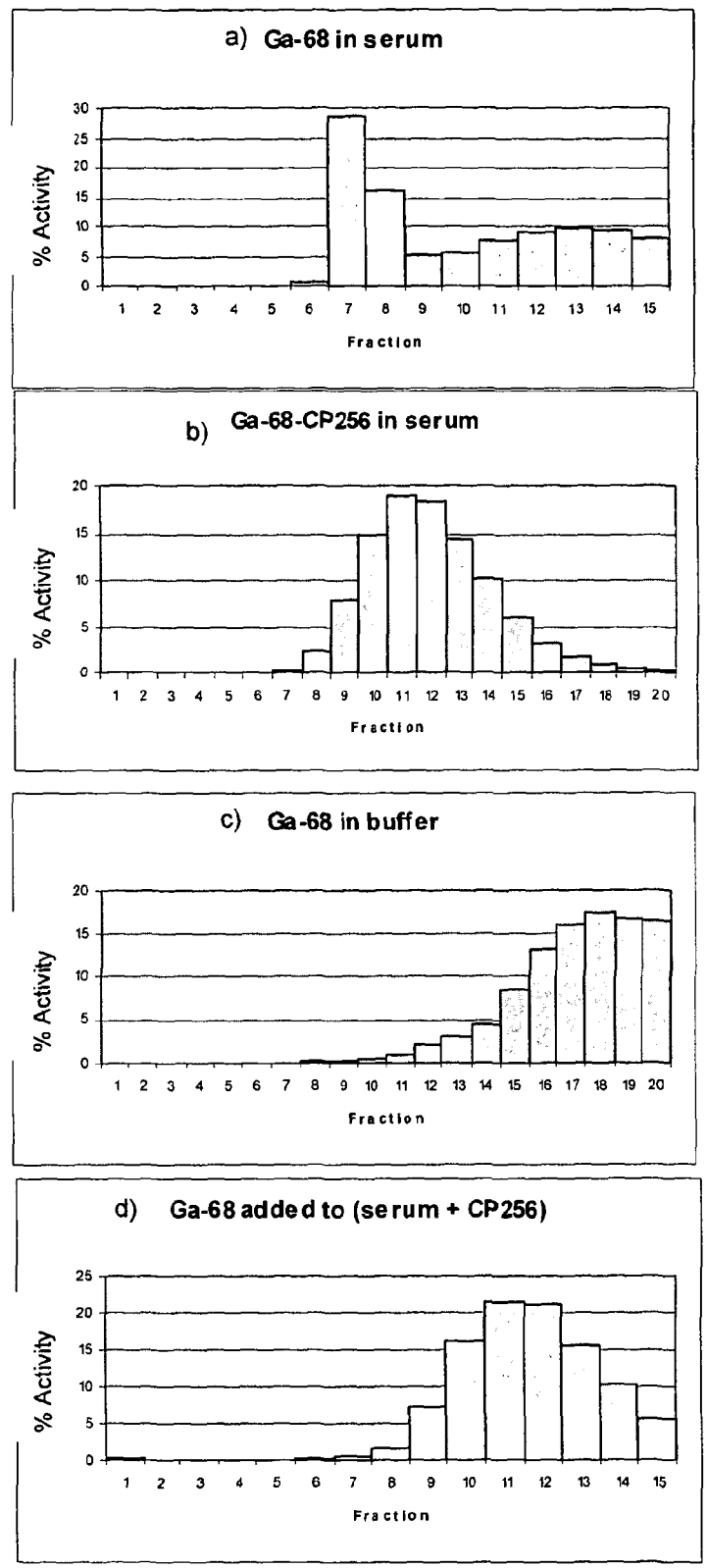
FIG. 7. Size exclusion radiochromatography (PD10 column) showing chelation of $^{68}$Ga by CP256 in serum: a) control, $^{68}$Ga chloride incubated in serum; b) control, preformed $^{68}$Ga-CP256 complex incubated with serum; c) control, $^{68}$Ga incubated in buffer; and d) experimental sample, $^{68}$Ga chloride added to serum to which CP256 (23 μM or above) had been added.

FIG. 7 shows size exclusion radiochromatography (PD10 column) of chelation of $^{68}$Ga by CP256 in serum and control experiments to show $^{68}$Ga-chloride incubated in serum, preformed $^{68}$Ga-CP256-(7) complex incubated with serum and $^{68}$Ga incubated in buffer.

As a measure of the efficiency of chelation of $^{68}$Ga with CP256, and to demonstrate the feasibility of the pre-targeting approach described above, the labelling was conducted in serum thus presenting the chelation process with challenge from serum transferrin. Addition of $^{68}$Ga chloride to a mixture of CP256 and serum gave a size exclusion chromatogram similar to that of $^{68}$Ga-CP256 when the CP256 sample concentration was 23 µM or above, whereas addition of $^{68}$Ga to serum alone gave a chromatogram consistent with a mixture of $^{68}$Ga-transferrin complex and "free" gallium. This shows that CP256 competes effectively with serum transferrin. Moreover, if the $^{68}$Ga was equilibrated first with serum, and then CP256 was added, again a chromatogram similar to that of $^{68}$Ga-CP256 was observed, showing that CP256 is able to extract $^{68}$Ga from $^{68}$Ga-transferrin complex. The ethanol precipitation and ITLC experiments confirmed that in serum containing CP256, there was no measurable protein binding and no detectable free $^{68}$Ga. All $^{68}$Ga remained at the origin on ITLC of the supernatants. These observations suggest that $^{68}$Ga and CP256 conjugates could be used in a novel "pretargeting" mode in vivo, whereby a targeted CP256 conjugate is administered and allowed to bind to target, followed by injection of $^{68}$Ga to locate the pretargeted CP256.

Experimental Details

Two different radiolabelling techniques were used. In method 1, 100 µl of chelator (CP-256, 2.35 mM, 1.17 mM, 589 µM, 117 µM, 23 µM and 11.7 µM; pH 7-7.5 in PBS/bicarbonate buffer) was mixed with 300 µl of human serum. After 10-15 minutes 20 µl of 68Ga eluate was added and the solution incubated at 37° C. in a plastic tube. In the second method, 20 µl of $^{68}$Ga solution was added to the 300 µl of human blood serum. After 15-20 minutes 100 µl of chelator (Cp-256) was added. At each time point 50 µl of the incubation solution was applied to the top of the PD-10 column and eluted the column with PBS collecting 0.5 ml fractions. Fractions were counted in a gamma counter (Perkin Elmer wizard 31480 automatic gamma counter, 10 seconds per sample). The incubated solution were also analysed by ethanol precipitation, counting the pellet and supernatant after centrifugation to determine protein bound $^{68}$Ga, and the centrifuged supernatants were analysed by ITLC-SG with 0.1 M sodium citrate as mobile phase. In these conditions "free" $^{68}$Ga migrates with the solvent front (Rf=1) and $^{68}$Ga-CP256 remains at the origin (Rf=0).

Example 10

Figure 8:
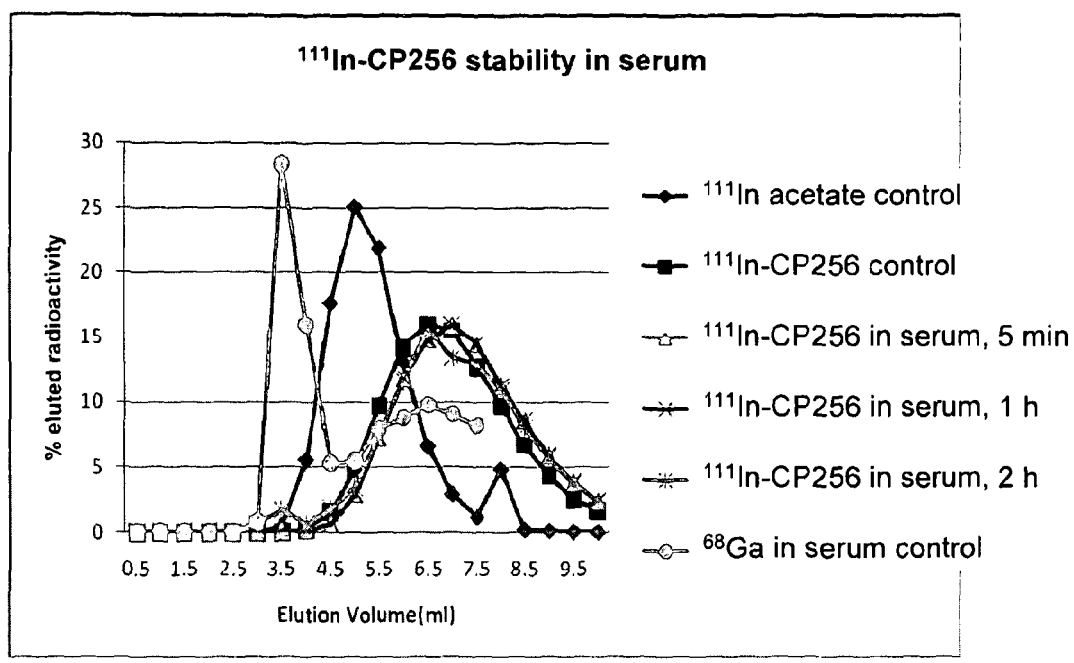
FIG. 8. PD10 size exclusion chromatography profile of $^{111}$In after incubation of $^{111}$In-acetate and $^{111}$In-CP256 in serum, compared to $^{111}$In-CP256 in buffer.

Labelling of CP256 with $^{111}$In $^{111}$In-chloride formed a complex with CP256 (589 µM) in about 90% yield after 5 min, as determined by ITLC-SG (HSA). The complex showed <2% release of In-111 or binding to serum proteins when incubated in human serum for 2 h, as determined by PD10 size exclusion chromatography (FIG. 8).

Experimental Details

A 50 µl aliquot of acetate buffer (pH=6) was added to vial containing $^{111}$InCl$_3$ (7 MBq, Mallinckrodt Medical) in HCl. A 589 µM solution of CP256 was prepared by dissolving 0.5 mg of CP256 in 1 ml of PBS. A 100 µl aliquot of this CP256 solution was mixed with 50 µl of the $^{111}$In solution. After incubation for 5 minutes the speciation of $^{111}$In was analysed using ITLC-SG strips that had been previously saturated with human serum albumin (HSA) and dried. The chromatograms were developed with water, ethanol and ammonia in the ratio of 5:2:1. Under these conditions $^{111}$In stays at the origin whereas $^{111}$In-CP256 moves to the solvent front.

Example 11

In Vivo Imaging of Antibody-CP256 Conjugate Via the Pretargeting Mode with $^{67}$Ga A monoclonal IgG antibody, SER4, against a sialoadhesin antigen expressed by pro-inflammatory macrophages, was conjugated with CP256-malemide (7) by first reducing antibody disulfide bonds with 2-mercaptoethanol, then treating the thiol groups so formed with CP256-maleimide (7) to give CP256-SER4.

The typical biodistribution in mice of SER4 labelled with $^{99m}$TC (unpublished data) observed previously reflects rapid clearance from circulation with uptake predominantly in spleen and to some extent also liver.

CP256-SER4 was labelled with $^{67}$Ga to give $^{67}$Ga-CP256-SER4. Groups of wild type mice were injected with either directly labelled Ga-CP256-SER4 (group 1), or SER4 (unconjugated) followed 5 min later by $^{67}$Ga citrate (group 2) or CP256-SER4 followed by $^{67}$Ga citrate.

The same experiments were also performed using sialoadhesin knockout mice. All animals were killed after 3 h and biodistribution of radioactivity determined.

Figure 9:
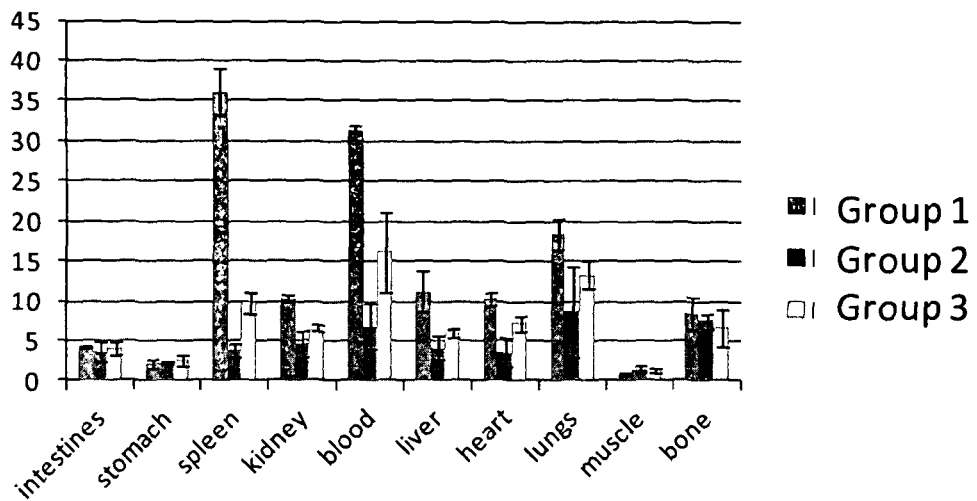
FIG. 9. Biodistribution of $^{67}$Ga-CP256-SER4 (Group 1), 67Ga-citrate 5 min after injection of SER4 (Group 2), and 67Ga-citrate 5 min after injection of CP256-SER4 (Group 3), in wild type mice (top) or sialoadhesin knockout mice (bottom).
Figure 9:
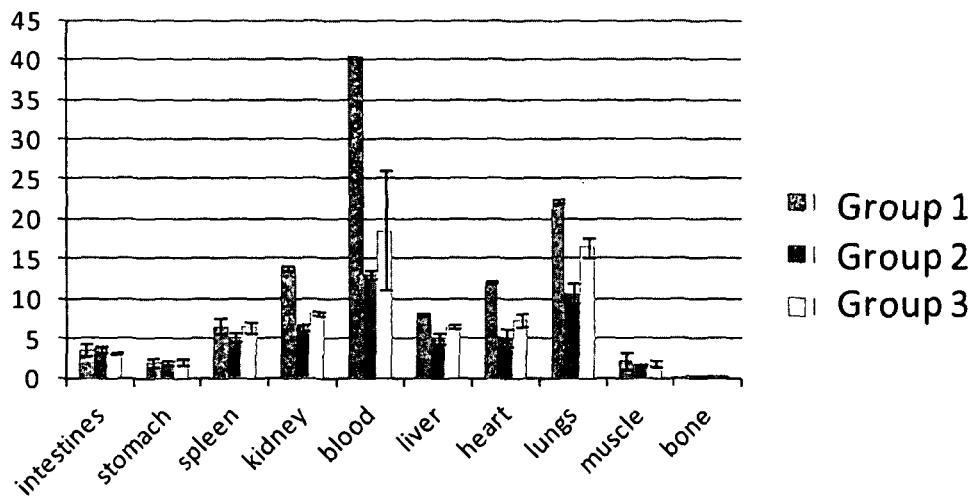

The results are shown in FIG. 9. For each organ, biodistribution data for Group 1 are shown in left hand column, biodistribution data for Group 2 are shown in the central column, and biodistribution data for Group 3 are shown in the right hand column.

Group 1 showed strong targeting of $^{67}$Ga-CP256-SER4 to spleen (36% ID/g), whereas group 2 showed very low spleen uptake of $^{67}$Ga citrate (4% ID/g). On the other hand, group 3 showed that pre-injection of CP256-SER4 was able to increase spleen uptake of $^{67}$Ga citrate from 4% ID/g to 10% ID/g, suggesting that the $^{67}$Ga followed the location of antibody conjugate to a significant extent.

Group 1 also showed high activity of $^{67}$Ga-CP256-SER4 in circulating blood (31% ID/g), whereas $^{67}$Ga-citrate (group 2) did not (7% ID/g); Pre-administration of CP256-SER4 (group 3) increased blood pool retention from 7% to 16% ID/g. The knockout mice did not show the spleen targeting behaviour, consistent with this pattern being associated with sialoadhesin expression. These experiments demonstrate the feasibility of imaging pretargeted unlabelled bioconjugates of CP256 by later injections of $^{67}$Ga citrate.

Experimental Details

For the conjugation of CP256 to SER4: To 2 mg (5 mg/mL) of SER4 antibody in phosphate buffered saline was added 25 µL of 50 mm EDTA. The resulting solution was left at room temperature for 1 h in order to chelate metal ions present in the solution.

The antibody was then washed by centrifugation at 3000 rpm for 3×15 min in a 50,000 mwco Vivaspin2 ultracentrifugation tube. The antibody was resuspended between centrifugation steps and the volume adjusted to 2 ml by addition of 0.1M metal-free phosphate buffer, pH 7. The concentrated and washed antibody was collected in approximately 300 µL 0.1 M phosphate buffer.

For the reduction of the antibody, 2-mercaptoethanol (5 µL) was diluted to 20 µL in 0.1 M phosphate buffer, pH 7. 3.8 µL (1000 fold excess) of the diluted 2-mercaptoethanol was added to the antibody and the reduction allowed to proceed for 30 min at room temperature.

The volume was adjusted to 1 ml by addition of 0.1 M phosphate buffer and the removed by applying the reduced antibody to a disposable size exclusion column (PD10). Fractions containing the reduced antibody were combined and CP256-maleimide (0.77 mg dissolved in 8 µL DMSO, a 40 fold excess) was added immediately. The conjugation reaction was heated at 37° C. for 30 min. The conjugated antibody was then washed using a 50,000 mwco Vivaspin2 ultracentrifugation tube as before but using 0.1 M ammonium acetate buffer, pH6 to remove the excess ligand. The concentrated CP256-antibody was collected in 0.1 M ammonium acetate buffer, pH6.

$^{67}$Gallium radiolabelling was performed by addition of 45 µL $^{67}$Ga citrate (0.6-0.75 MBq) to 90 µL (90 µg) CP256-SER4. Radiolabelling was allowed to proceed for 10 min before dilution to 350 µL with phosphate buffered saline. Injections containing 25 µg of labelled antibody were drawn up. Analysis of the radiolabelled antibody was performed by size exclusion HPLC using 0.1 M phosphate buffer containing 2 mM EDTA as the mobile phase to ensure good radiolabelling had been achieved prior to injection into animals.

Groups of wild type mice (C57Bl/6, male 8-10 weeks, n=2 to 3 per group) were injected with either directly labelled $^{67}$Ga-CP256-SER4 (group 1), or SER4 (unconjugated) followed 5 min later by $^{67}$Ga citrate (group 2) or CP256-SER4 followed by ⁶⁷Ga citrate. The activity of ⁶⁷Ga and the amount of antibody used in each case was equivalent. The same experiments were also performed using knockout mice (Sialoadhesin KO, C57Bl/6, male 8-10 weeks, n=2 to 3 per group). All animals were killed after 3 h and biodistribution of radioactivity determined by explanting tissues and weighing and counting.

Example 12

In Vivo Imaging of Antibody-CP256 Conjugate Via the Pretargeting Mode with ⁶⁸Ga

SER4, conjugated with CP256-malemide (7) as described in Example 11, was labelled with ⁶⁸Ga as described above in example 7, to give ⁶⁸Ga-CP256-SER4. On three separate occasions groups of wild type mice (C57Bl/6, male 8-10 weeks, n=2 to 3 per group) were injected with either ⁶⁸Ga-CP256-SER4 (group 1), or SER4 (unconjugated) followed 1 h later by ⁶⁸Ga acetate (group 2) or CP256-SER4 followed 1 h later by ⁶⁸Ga acetate (group 3).

Figure 10:
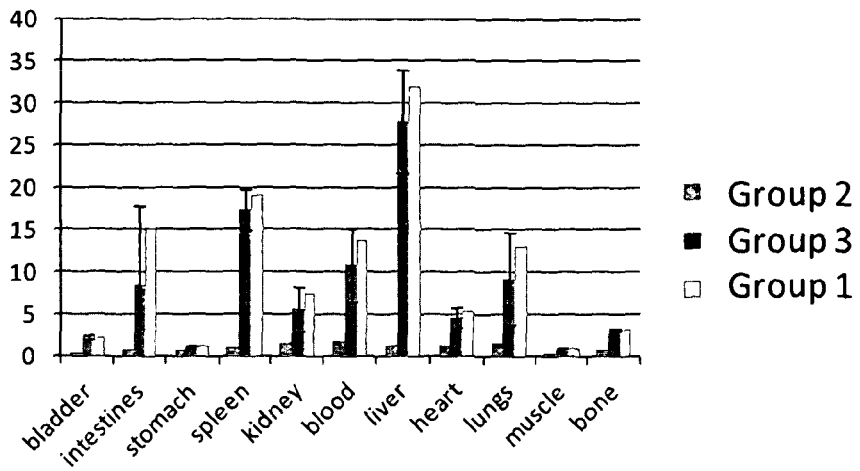
FIG. 10. Biodistribution of $^{68}$Ga-CP256-SER4 (Group 1), $^{68}$Ga acetate injected 1 h after injection of SER4 (Group 2), and $^{68}$Ga acetate injected 1 h after injection of CP256-SER4 (Group 3), in wild type mice.
Figure 10:
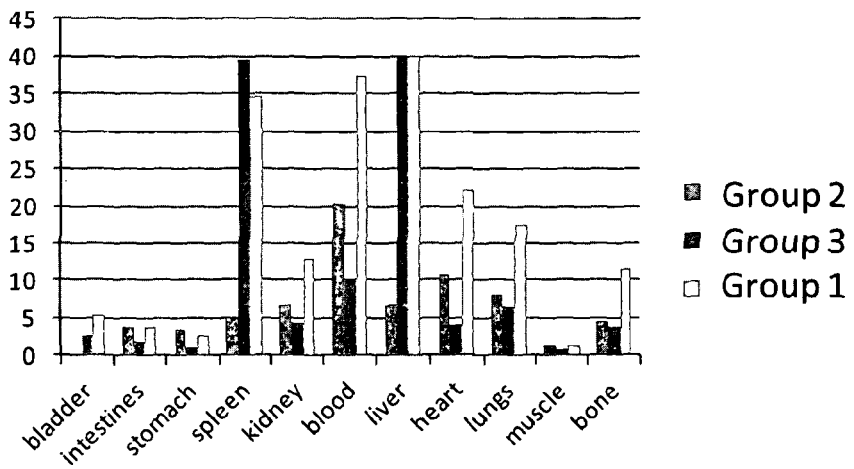
Figure 10:
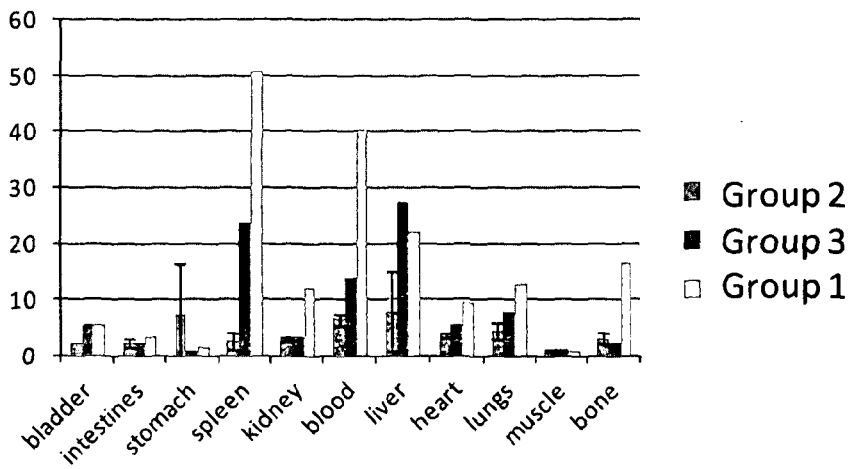

All animals were killed 1.5 h after injection of ⁶⁸Ga and biodistribution of radioactivity determined. The results are shown in FIG. 10. For each organ, biodistribution data for Group 2 are shown in left hand column, biodistribution data for Group 3 are shown in the central column, and biodistribution data for Group 1 are shown in the right hand column.

Group 1 showed strong targeting of ⁶⁸Ga-CP256-SER4 to spleen (20-50% ID/g over the three experiments), whereas group 2 showed very low spleen uptake of ⁶⁸Ga acetate (2-5% ID/g). On the other hand, group 3 showed that pre-injection of CP256-SER4 was able to increase spleen uptake of ⁶⁸Ga acetate from 2-5% ID/g to 17-40% ID/g, suggesting that the ⁶⁸Ga followed the location of antibody conjugate to a significant extent. These experiments demonstrate the feasibility of imaging pretargeted unlabelled bioconjugates of CP256 by later injections of ⁶⁸Ga acetate.

Figure 11:
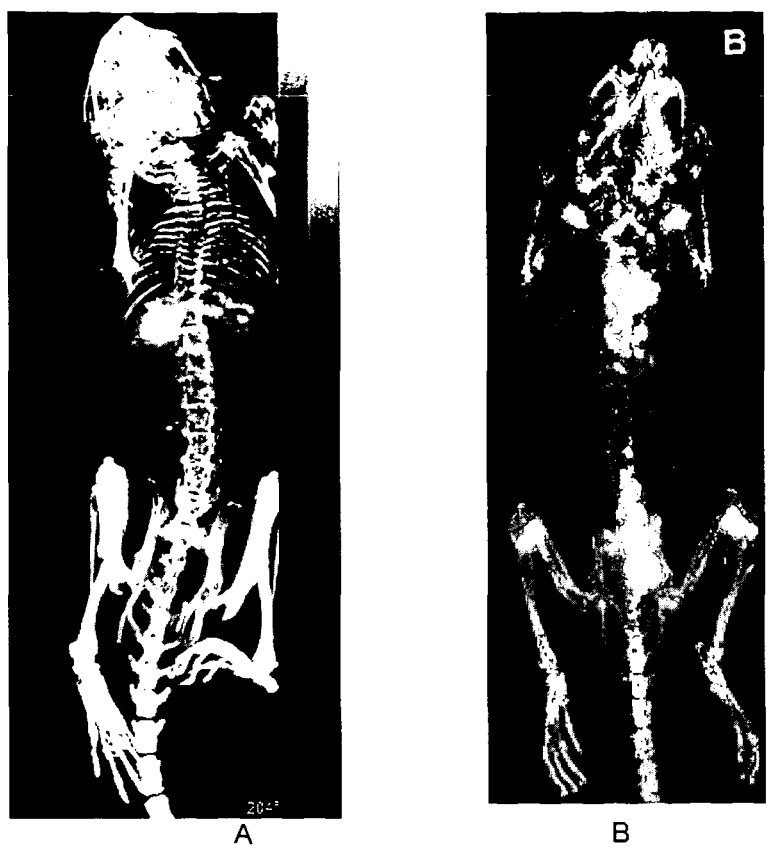
FIG. 11.

A NanoPET/CT image of a mouse from group 3 is shown in FIG. 11A. The mouse was image using the pre-targeting method of the invention using CP256-SER4: 8 week-old C57Bl/6 injected with CP256-SER4 followed by Ga-68 acetate. The figure shows targeted liver/spleen uptake. For comparison, a mouse injected with Ga-68 acetate only is shown in FIG. 11B, showing retention in blood pool and accumulation in joints.

Experimental Details

The antibody was conjugated to CP256 as described in Example 11. For radiolabelling, ⁶⁸Ga was eluted from a ⁶⁸Ge/⁶⁸Ga generator and concentrated as described in Example 7 to give ⁶⁸Ga acetate. To 150 μL (105 μg) CP256-SER4 was added 150 μL ⁶⁸Ga acetate (16 MBq). The radiolabelling reaction was allowed to proceed for 5 min at room temperature. Injections containing 35 μg of the radiolabelled antibody were drawn up. Analysis of the radiolabelled antibody was carried out as described in Example 11.

Groups of wild type mice (C57Bl/6, male 8-10 weeks, n=2 to 3 per group) were injected with either directly labelled ⁶⁸Ga-CP256-SER4 (group 1), or SER4 (unconjugated) followed 1 h later by ⁶⁸Ga acetate (group 2) or CP256-SER4 followed by ⁶⁸Ga acetate. The activity of ⁶⁸Ga and the amount of antibody used in each case was equivalent. All animals were killed after 2-3 h and biodistribution of radioactivity determined by explanting tissues and weighing and counting. One animal from each group was scanned using a NanoPET/CT scanner (Bioscan). Scans were initiated immediately after injection of ⁶⁸Ga acetate or ⁶⁸Ga-CP256-SER4 and continued for 1.5 h.

REFERENCES

The following references are expressly incorporated by reference for all purposes in their entirety.
1. Emberson et al., J. Immunol. Methods. 305(2):135-51, 2005
2. Giersing et al., Bioconjug Chem. 12(6): 964-71, 2001
3. Bird et al, Science, 242; 423-426, 1988
4. Huston et al, PNAS USA, 85: 5879-5883, 1988
5. Holliger et al, P.N.A.S. USA, 90: 6444-6448, 1993
6. Reiter et al, Nature Biotech, 14: 1239-1245, 1996
7. Hu et al, Cancer Res., 56: 3055-3061, 1996
8. Newkome et al., *J Org Chem,* 1991, 56, 7162-7167
9. Zhou T. et al., J Med. Chem. 2006, 49, 4171-4182
10. Tavare et al., Bioconjugate Chem 2009; 20:2071-2081
11. Tait et al., Anal. Biochem. 329, 112-119

We claim:

1. A bifunctional compound precursor, a bifunctional compound or a bifunctional molecule, wherein:
(a) the bifunctional compound precursor is represented by the formula:

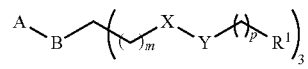

or salts thereof;
wherein one of X and Y is C=O and the other is NR;
provided that if one of X and Y is C=O and the other is NR, then m is selected from 0 to 6, and p is selected from 1 to 6;
wherein $R^1$ is a chelating group capable of chelating a radionuclide and is selected from:

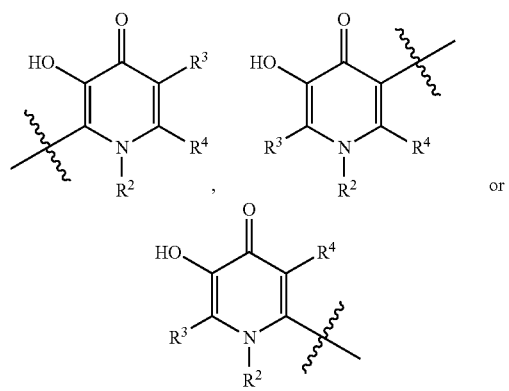

wherein R, $R^2$, $R^3$ and $R^4$ are independently hydrogen or an optionally substituted $C_{1-7}$ alkyl group;
B is a linker group for linking the chelating group to the reactive group, and is represented by the formula:

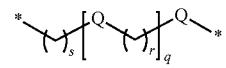

wherein each Q is independently selected from a group consisting of —$NR^5$—, —C(O)$NR^5$—, —C(O)O—, —$NR^5$C (O)NR$^5$—, —NR$^5$C(S)NR$^5$— and —O—, each R$^5$ is independently hydrogen or an optionally substituted C$_{1-7}$ alkyl group, each q and s are independently selected from 0 to 6 and each r is independently selected from 1 to 6;

A is a reactive group for coupling to a biological moiety, a targeting group, a protein, a polypeptide or a delivery vehicle;

(b) the bifunctional compound is represented by the formula:

or salts thereof;

wherein one of X and Y is C=O and the other is NR;

provided that if one of X and Y is C=O and the other is NR, then m is selected from 0 to 6, and p is selected from 1 to 6;

wherein R$^1$ is a chelating group capable of chelating a radionuclide and is selected from:

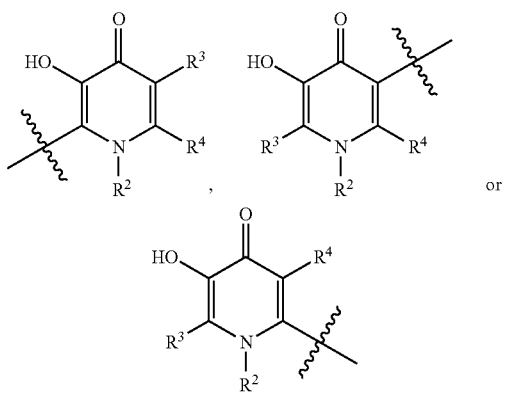

wherein R, R$^2$, R$^3$ and R$^4$ are independently hydrogen or an optionally substituted C$_{1-7}$ alkyl group;

B is a linker group for linking the chelating group to the reactive group, and is represented by the formula:

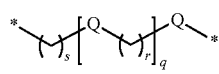

wherein each Q is independently selected from a group consisting of —NR$^5$—, —C(O)NR$^5$—, —C(O)O—, —NR$^5$C(O)NR$^5$—, —NR$^5$C(S)NR$^5$— and —O—, each R$^5$ is independently hydrogen or an optionally substituted C$_{1-7}$ alkyl group, each q and s are independently selected from 0 to 6 and each r is independently selected from 1 to 6;

A* is a reacted reactive group that is coupled to T, T being a targeting group capable of binding to a target of interest in a subject; or (c) the bifunctional molecule comprises a bifunctional compound and a radionuclide bound through a chelating group of the bifunctional compound, wherein the bifunctional compound of the bifunctional molecule is represented by the formula:

or salts thereof;

wherein one of X and Y is C=O and the other is NR;

provided that if one of X and Y is C=O and the other is NR, then m is selected from 0 to 6, and p is selected from 1 to 6;

wherein R$^1$ is a chelating group capable of chelating a radionuclide and is selected from:

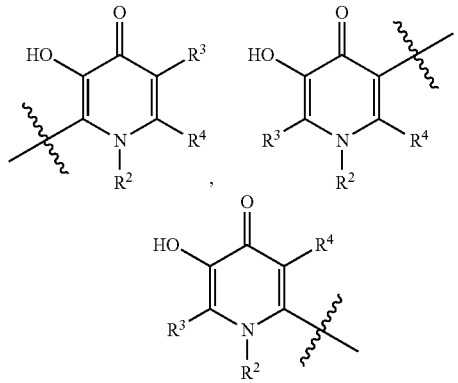

wherein R, R$^2$, R$^3$ and R$^4$ are independently hydrogen or an optionally substituted C$_{1-7}$ alkyl group;

B is a linker group for linking the chelating group to the reactive group, and is represented by the formula:

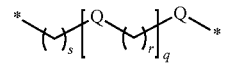

wherein each Q is independently selected from a group consisting of —NR$^5$—, —C(O)NR$^5$—, —C(O)O—, —NR$^5$C(O)NR$^5$—, —NR$^5$C(S)NR$^5$— and —O—, each R$^5$ is independently hydrogen or an optionally substituted C$_{1-7}$ alkyl group, each q and s are independently selected from 0 to 6 and each r is independently selected from 1 to 6;

A* is a reacted reactive group that is coupled to T, T being a targeting group capable of binding to a target of interest in a subject.

2. The bifunctional compound precursor, bifunctional compound or bifunctional molecule according to claim 1, wherein s is independently selected from 0 to 6, each r is independently selected from 1 to 6, and q is selected from 1 to 6.

3. The bifunctional compound precursor, bifunctional compound or bifunctional molecule according to claim 1, wherein the reactive group A is a protein-reactive functional group selected from the group consisting of a maleimide, aldehyde, ester, hydrazine, hydrazine derivative, alkoxyamine, alkoxyamine derivative, alkyne, alkene and azide group.

4. The bifunctional compound precursor, bifunctional compound or bifunctional molecule according to claim 1, wherein R$^1$ is

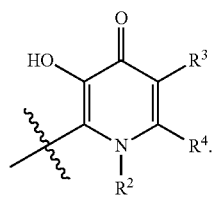

5. The bifunctional compound precursor, bifunctional compound or bifunctional molecule according to claim 1, which comprises a bifunctional compound or bifunctional molecule, and comprising a bifunctional compound represented by the formula:

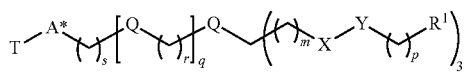

wherein T, A*, Q, X, Y, R¹, s, p, q, r and m are as defined in claim 1.

6. The bifunctional compound precursor, bifunctional compound or bifunctional molecule according to claim 1, wherein B is represented by one of the following formula:

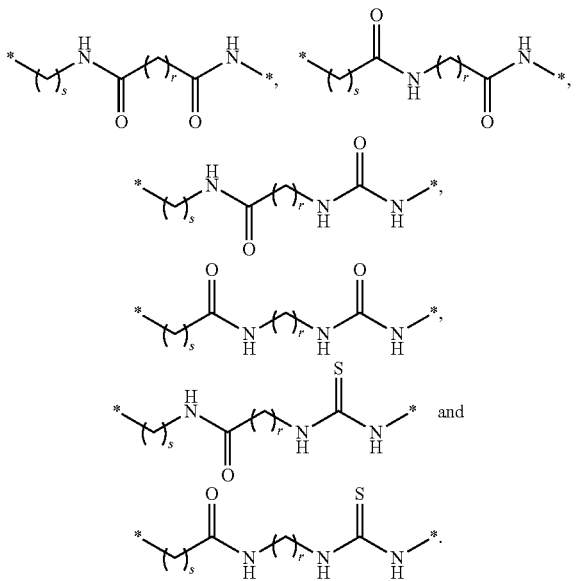

wherein s and r are as defined in claim 1.

7. The bifunctional precursor, bifunctional compound or bifunctional molecule according to claim 1 which is a bifunctional molecule, wherein the radionuclide is an isotope of scandium, iron, cobalt, copper, gallium, yttrium, zirconium, technetium, indium, tin, rhenium, gadolinium, terbium, holmium, bismuth, or lutetium.

8. The bifunctional molecule according to claim 7, wherein the radionuclide is Ga-68, Ga-67, or Bi-213.

9. The bifunctional compound precursor, bifunctional compound or bifunctional molecule according to claim 1, wherein the targeting group is a member of a specific binding pair that is capable of binding to a binding partner at the target of interest.

10. The bifunctional compound precursor, bifunctional compound or bifunctional molecule according claim 1 which is a bifunctional compound or bifunctional molecule, wherein the targeting group T and target of interest are a receptor and ligand, or an antibody and antigen, or metabolic probe.

11. The bifunctional compound precursor, bifunctional compound or bifunctional molecule according to claim 1 which is a bifunctional compound or bifunctional molecule, wherein the targeting group T is a peptide, protein, antibody, aptamer or small molecule ligand capable of binding to binding partner at the target of interest.

12. The bifunctional compound precursor, bifunctional compound or bifunctional molecule according to claim 11, wherein the targeting group T includes Annexin V and the C2 domain of a synaptotagmin, TIMP-2, CEA, RGD peptide, somatostatin receptor targeting peptide, bombesin, gastrin or VCAM targeting peptide.

13. The bifunctional compound precursor, bifunctional compound or bifunctional molecule according to claim 1 which is a bifunctional compound or bifunctional molecule, wherein the target of interest is a ligand or receptor expressed on diseased cells or tissue, a cell surface antigen associated with a disease state, or tumour markers.

14. The bifunctional compound precursor, bifunctional compound or bifunctional molecule according to claim 1 which is a bifunctional compound or bifunctional molecule, wherein the target of interest is a location, an organ, a tissue type, infectious agent or physiological property in a subject undergoing molecular imaging.

15. The bifunctional compound precursor, bifunctional compound or bifunctional molecule according to claim 1, wherein the compound further includes a secondary imaging label.

16. The bifunctional compound precursor, bifunctional compound or bifunctional molecule according to claim 1, which comprises a bifunctional compound precursor represented by the formula:

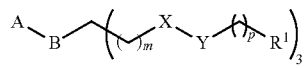

or salts thereof;
wherein one of X and Y is C=O and the other is NR;
provided that either (i) if one of X and Y is C=O and the other is NR, then m is selected from 0 to 6, and p is selected from 1 to 6;
wherein R¹ is a chelating group capable of chelating a radionuclide and is selected from:

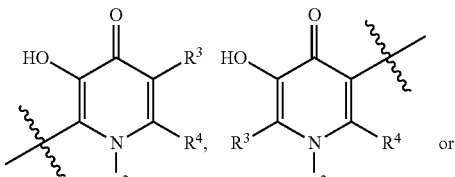

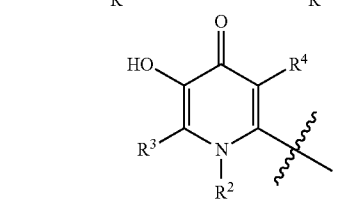

wherein R, R², R³ and R⁴ are independently hydrogen or an optionally substituted $C_{1-7}$ alkyl group;

B is a linker group for linking the chelating group to the reactive group, and is represented by the formula:

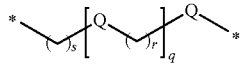

wherein each Q is independently selected from a group consisting of —NR⁵—, —C(O)NR⁵—, —C(O)O—, —NR⁵C(O)NR⁵—, —NR⁵C(S)NR⁵— and —O—, each R⁵ is independently hydrogen or an optionally substituted $C_{1-7}$ alkyl group, each q and s are independently selected from 0 to 6 and each r is independently selected from 1 to 6;

A is a reactive group for coupling to a biological moiety, a targeting group, a protein, a polypeptide or a delivery vehicle.

17. The bifunctional compound precursor, bifunctional compound or bifunctional molecule according to claim 1, which comprises a bifunctional compound represented by the formula:

or salts thereof;

wherein one of X and Y is C=O and the other is NR;

provided that either (i) if one of X and Y is C=O and the other is NR, then m is selected from 0 to 6, and p is selected from 1 to 6;

wherein R¹ is a chelating group capable of chelating a radionuclide and is selected from:

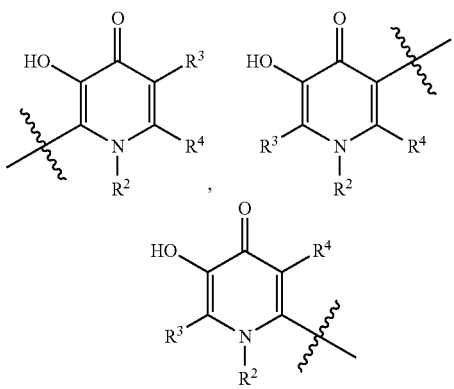

wherein R, R², R³ and R⁴ are independently hydrogen or an optionally substituted $C_{1-7}$ alkyl group;

B is a linker group for linking the chelating group to the reactive group, and is represented by the formula:

wherein each Q is independently selected from a group consisting of —NR⁵—, —C(O)NR⁵—, —C(O)O—, —NR⁵C(O)NR⁵—, —NR⁵C(S)NR⁵— and —O—, each R⁵ is independently hydrogen or an optionally substituted $C_{1-7}$ alkyl group, each q and s are independently selected from 0 to 6 and each r is independently selected from 1 to 6;

A* is a reacted reactive group that is coupled to T, T being a targeting group capable of binding to a target of interest in the subject.

18. The bifunctional compound precursor, bifunctional compound or bifunctional molecule according to claim 1, which comprises a bifunctional molecule comprising a bifunctional compound and a radionuclide bound through a chelating group of the bifunctional compound, wherein the bifunctional compound of the bifunctional molecule is represented by the formula:

or salts thereof;

wherein one of X and Y is C=O and the other is NR;

provided that either (i) if one of X and Y is C=O and the other is NR, then m is selected from 0 to 6, and p is selected from 1 to 6;

wherein R¹ is a chelating group capable of chelating a radionuclide and is selected from:

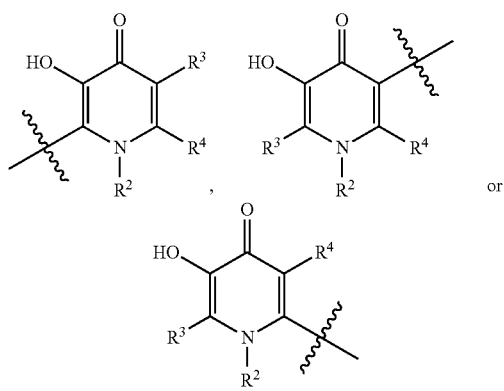

wherein R, R², R³ and R⁴ are independently hydrogen or an optionally substituted $C_{1-7}$ alkyl group;

B is a linker group for linking the chelating group to the reactive group, and is represented by the formula:

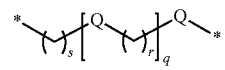

wherein each Q is independently selected from a group consisting of —NR⁵—, —C(O)NR⁵—, —C(O)O—, —NR⁵C(O)NR⁵—, —NR⁵C(S)NR⁵— and —O—, each R⁵ is independently hydrogen or an optionally substituted $C_{1-7}$ alkyl group, each q and s are independently selected from 0 to 6 and each r is independently selected from 1 to 6;

A* is a reacted reactive group that is coupled to T, T being a targeting group capable of binding to a target of interest in the subject.

19. The bifunctional compound precursor, bifunctional compound, or bifunctional molecule according to claim 1, wherein
m=2; p=1;
Y is NR and X is C=O;
$R^1$ is

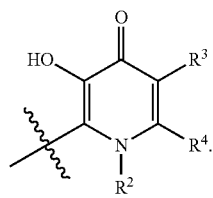

or salt thereof; and
$R^2$, $R^3$ and $R^4$ are independently hydrogen or $CH_3$.

20. The bifunctional compound precursor, bifunctional compound or bifunctional molecule according to claim 1, wherein the group

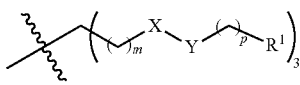

is represented by the group

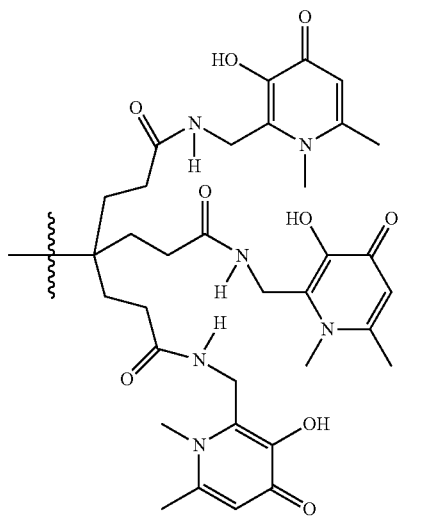

or

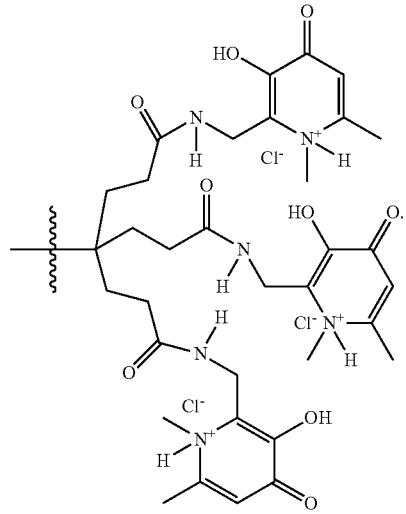

21. The bifunctional compound precursor, bifunctional compound or bifunctional molecule according to claim 1, which comprises a bifunctional compound precursor of formulae:

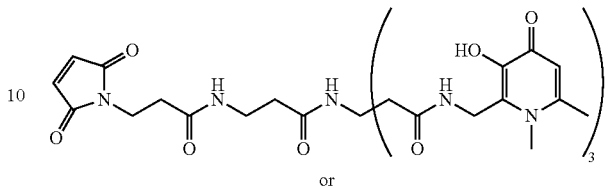

or

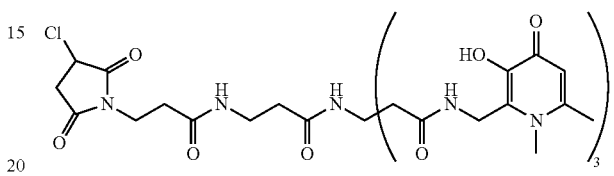

or salts thereof.

22. The bifunctional compound precursor, bifunctional compound or bifunctional molecule according to claim 1, which comprises a bifunctional compound or bifunctional molecule wherein the bifunctional compound is represented by the formula:

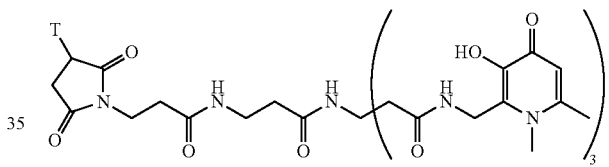

or salts thereof.

23. A kit for use in a method of molecular imaging or therapy comprising: a bifunctional compound composition having a bifunctional compound represented by the formula:

or salts thereof;
wherein one of X and Y is C=O and the other is NR;
provided that if one of X and Y is C=O and the other is NR, then m is selected from 0 to 6, and p is selected from 1 to 6;
wherein $R^1$ is a chelating group capable of chelating a radionuclide and is selected from:

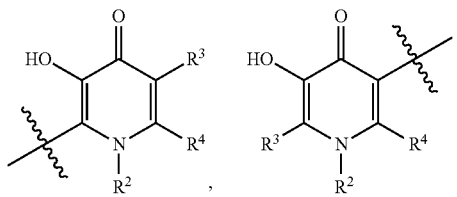

or

-continued

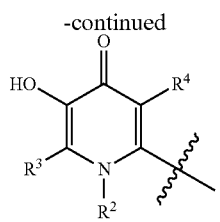

wherein R, $R^2$, $R^3$ and $R^4$ are independently hydrogen or an optionally substituted $C_{1-7}$ alkyl group;

B is a linker group for linking the chelating group to the reactive group, and is represented by the formula:

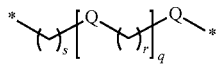

wherein each Q is independently selected from a group consisting of —$NR^5$—, —C(O)$NR^5$—, —C(O)O—, —$NR^5$C(O)$NR^5$—, —$NR^5$C(S)$NR^5$— and —O—, each $R^5$ is independently hydrogen or an optionally substituted $C_{1-7}$ alkyl group, each q and s are independently selected from 0 to 6 and each r is independently selected from 1 to 6;

A* is a reacted reactive group that is coupled to T, T being a targeting group capable of binding to a target of interest in the subject; and an imaging composition comprising a radionuclide.

24. A method of therapy or molecular imaging a target of interest in a biological system, the method comprising:
(a) administering to a subject a bifunctional compound composition comprising a bifunctional compound represented by the formula:

or salts thereof;
wherein one of X and Y is C═O and the other is NR;
provided that if one of X and Y is C═O and the other is NR, then m is selected from 0 to 6, and p is selected from 1 to 6;
wherein $R^1$ is a chelating group capable of chelating a radionuclide and is selected from:

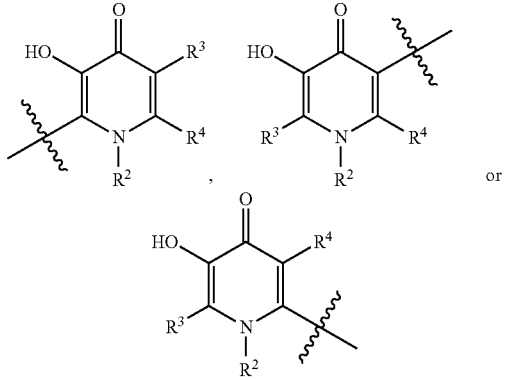

wherein R, $R^2$, $R^3$ and $R^4$ are independently hydrogen or an optionally substituted $C_{1-7}$ alkyl group;

B is a linker group for linking the chelating group to the reactive group, and is represented by the formula:

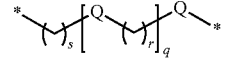

wherein each Q is independently selected from a group consisting of —$NR^5$—, —C(O)$NR^5$—, —C(O)O—, —$NR^5$C(O)$NR^5$—, —$NR^5$C(S)$NR^5$— and —O—, each $R^5$ is independently hydrogen or an optionally substituted $C_{1-7}$ alkyl group, each q and s are independently selected from 0 to 6 and each r is independently selected from 1 to 6;

A* is a reacted reactive group that is coupled to T, T being a targeting group capable of binding to a target of interest in the subject; and then (b) administering to the subject an imaging probe composition comprising a radionuclide, wherein the chelating group $R^1$ of the bifunctional compound is capable of chelating the radionuclide; or the method comprising:

(a) administering to a subject a bifunctional molecule composition comprising a bifunctional molecule, wherein the bifunctional molecule comprises a bifunctional compound and a radionuclide bound through a chelating group of the bifunctional compound, wherein the bifunctional compound of the bifunctional molecule is represented by the formula:

or salts thereof;
wherein one of X and Y is C═O and the other is NR;
provided that if one of X and Y is C═O and the other is NR, then m is selected from 0 to 6, and p is selected from 1 to 6;
wherein $R^1$ is a chelating group capable of chelating a radionuclide and is selected from:

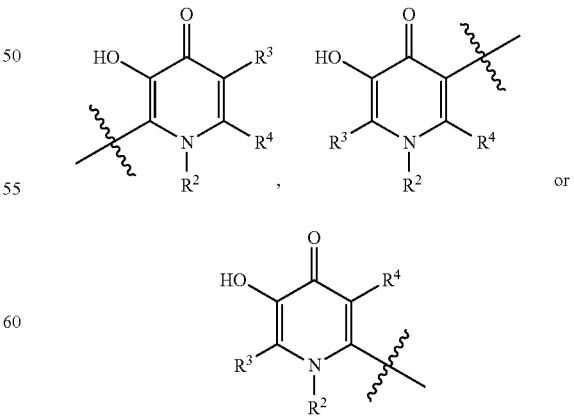

wherein R, $R^2$, $R^3$ and $R^4$ are independently hydrogen or an optionally substituted $C_{1-7}$ alkyl group;

B is a linker group for linking the chelating group to the reactive group, and is represented by the formula:

wherein each Q is independently selected from a group consisting of —$NR^5$—, —$C(O)NR^5$—, —$C(O)O$—, —$NR^5C(O)NR^5$—, —$NR^5C(S)NR^5$— and —O—, each $R^5$ is independently hydrogen or an optionally substituted $C_{1-7}$ alkyl group, each q and s are independently selected from 0 to 6 and each r is independently selected from 1 to 6;

A* is a reacted reactive group that is coupled to T, T being a targeting group capable of binding to a target of interest in the subject;

wherein the method of molecular imaging further comprises the step of detecting the radionuclide to image the target of interest in the biological system.

25. A method according to claim 24, wherein the biological system is a subject undergoing diagnosis or therapy for a disease or condition that comprises molecular imaging or therapy, or a subject in whom the biodistribution of the targeting molecule is being evaluated, and the therapy is radionuclide therapy or cancer treatment using a radionuclide or chemotherapeutic agent associated with the bifunctional compound.

26. The method according to claim 24, wherein the radionuclide is Sc-47, Cu-64, Cu-67, Ga-67, Ga-68, Zr-89, Y-90, In-111, Sn-117m, Tb-149, Gd-153, Ho-166, Lu-177, Re-186, Re-188, or Bi-213.

27. A gallium-ligand complex or use of a gallium-ligand complex in a method of claim 24, wherein the gallium-ligand complex comprises a ligand represented by one of the following formulae:

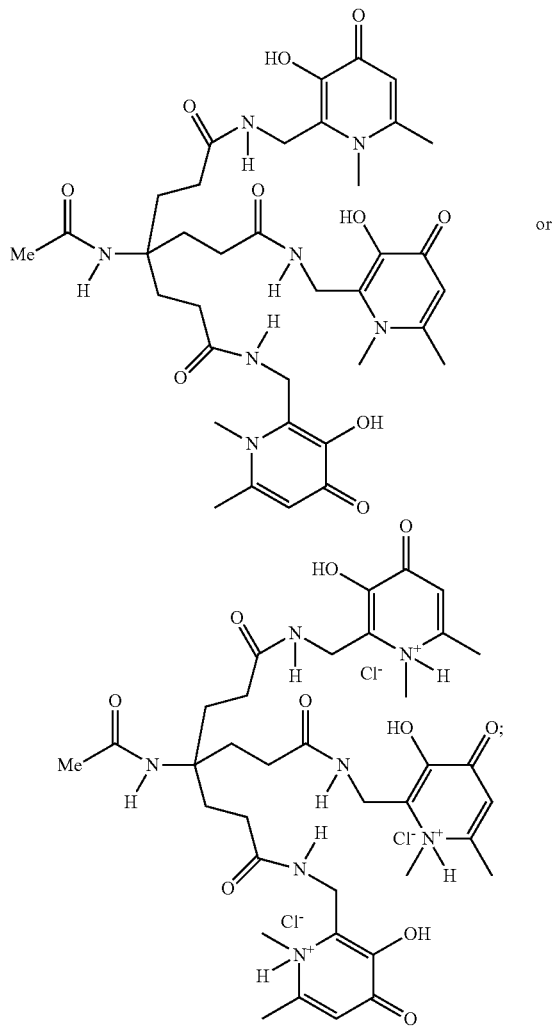

and a gallium isotope complexed to the ligand.

* * * * *